(12) United States Patent
Riemeier et al.

(10) Patent No.: US 10,130,987 B2
(45) Date of Patent: Nov. 20, 2018

(54) METHOD FOR CALIBRATION OF MANIPULATOR UTILIZED IN APPARATUS AND METHOD FOR CUSTOMIZED SHAPING OF ORTHODONTIC ARCHWIRES AND OTHER MEDICAL DEVICES

(71) Applicant: OraMetrix, Inc., Richardson, TX (US)

(72) Inventors: Friedrich Riemeier, Berlin (DE); Werner Butscher, Berlin (DE); Frank Witte, Berlin (DE); Christoph Radinger, Teltow (DE); Andrew Cordell, McKinney, TX (US); Rohit Sachdeva, Plano, TX (US)

(73) Assignee: OraMetrix, Inc., Richardson, TX (US)

( * ) Notice: Subject to any disclaimer, the term of this patent is extended or adjusted under 35 U.S.C. 154(b) by 107 days.

(21) Appl. No.: 14/990,375

(22) Filed: Jan. 7, 2016

(65) Prior Publication Data

US 2016/0114377 A1    Apr. 28, 2016

Related U.S. Application Data

(60) Division of application No. 13/621,848, filed on Sep. 18, 2012, now Pat. No. 9,610,628, which is a continuation of application No. 12/387,542, filed on May 4, 2009, now Pat. No. 8,266,940.

(51) Int. Cl.
*B21F 45/00* (2006.01)
*A61C 7/00* (2006.01)
(Continued)

(52) U.S. Cl.
CPC ............ *B21F 45/008* (2013.01); *A61C 7/002* (2013.01); *A61C 7/20* (2013.01); *B21F 1/008* (2013.01);
(Continued)

(58) Field of Classification Search
CPC .......... B21F 45/008; B21F 1/008; B21F 1/00; B21F 3/00; B21C 51/00; B21D 7/02;
(Continued)

(56) References Cited

U.S. PATENT DOCUMENTS 4,656,860 A    4/1987 Orthuber et al.
5,447,432 A    9/1995 Andreiko et al.
(Continued)

OTHER PUBLICATIONS

Denavit, J., Hartenberg, R. S.: A kinematic notation for lower pair mechanisms based on Matrices. Journal of Applied Mechanics, vol. 77, pp. 215-221, Jun. 1955.
(Continued)

*Primary Examiner* — Peter DungBa Vo
*Assistant Examiner* — John S Lowe
(74) *Attorney, Agent, or Firm* — McDonnell Boehnen Hulbert & Berghoff LLP

(57) ABSTRACT

An apparatus and method for bending or shaping orthodontic archwires or other medical devices into a complex, patient individual shape is described. The apparatus comprises of two moveable, compact, manipulators with, in total, at least three revolute joints defining three rotation axes and at least three prismatic joints defining at least three translation axes. Gripping tools are provided on the manipulators. The two manipulators are arranged to allow a relative movement in six degrees of freedom. A reduced complexity embodiment is also described having only one or two revolute joints.

9 Claims, 11 Drawing Sheets

(51) Int. Cl.
*B21C 51/00* (2006.01)
*B21F 1/00* (2006.01)
*B25J 9/16* (2006.01)
*A61C 7/20* (2006.01)
*G01B 11/24* (2006.01)

(52) U.S. Cl.
CPC ............ *B25J 9/1682* (2013.01); *G01B 11/24* (2013.01); *B21C 51/00* (2013.01); *G05B 2219/37426* (2013.01); *G05B 2219/45097* (2013.01); *G05B 2219/45167* (2013.01)

(58) Field of Classification Search
CPC ..... B21D 7/022; A61C 13/0004; A61C 7/002; A61C 7/20; A61C 7/02; G01B 11/24; G01B 11/03; G01B 21/04; G05B 2219/45167; G05B 2219/37205; G05B 11/32; Y10T 29/49568
USPC ...................................... 72/31.04, 31.05, 369
See application file for complete search history.

(56) References Cited

U.S. PATENT DOCUMENTS

| | | | |
|---|---|---|---|
| 6,612,143 B1 | 9/2003 | Butscher et al. | |
| 6,632,089 B2 | 10/2003 | Rubbert et al. | |
| 6,648,640 B2 | 11/2003 | Rubbert et al. | |
| 6,732,558 B2 | 5/2004 | Butscher et al. | |
| 6,755,064 B2 | 6/2004 | Butscher et al. | |
| 6,860,132 B2 | 3/2005 | Butscher et al. | |
| 7,076,980 B2 | 7/2006 | Butscher et al. | |
| 7,283,891 B2 | 10/2007 | Riemeier et al. | |
| 7,571,025 B2 * | 8/2009 | Bischoff | B25J 9/1682 219/121.6 |
| 8,047,034 B2 * | 11/2011 | Butscher | A61K 31/198 72/20.1 |
| 8,588,974 B2 * | 11/2013 | Aoba | B25J 9/1692 700/194 |
| 9,393,694 B2 * | 7/2016 | Wallack | B25J 9/1692 |
| 9,457,470 B2 * | 10/2016 | Lundberg | B25J 9/1692 |

OTHER PUBLICATIONS

J. Wittenburg and L. Lilov: "Decomposition of a Finite Rotation into Three Rotations about Given Axes", published in Journal Multibody System Dynamics by Springer Netherlands ISSN1384-5640 (Print) 1573-272X (Online) Issued in vol. 9, No. 4 / May 2003 DOI 10.1023/A:1023389218547 pp. 353-375).

Anthony A. Maciejewski and Charles A. Klein: "The Singular Value Decomposition: Computation and Applications to Robotics," published in: The International Journal of Robotics Research, vol. 8, No. 6, 63-79 (1989), DOI: 10.1177/027836498900800605).

* cited by examiner

METHOD FOR CALIBRATION OF MANIPULATOR UTILIZED IN APPARATUS AND METHOD FOR CUSTOMIZED SHAPING OF ORTHODONTIC ARCHWIRES AND OTHER MEDICAL DEVICES

CROSS-REFERENCE TO RELATED APPLICATIONS

This application is a divisional application of U.S. patent application Ser. No. 13/621,848 filed Sep. 18, 2012, which is a continuation application of the U.S. patent application Ser. No. 12/387,542 filed May 4, 2009, now issued as U.S. Pat. No. 8,266,940.

BACKGROUND

A. Field of the Invention

This invention relates to machines and methods for automatically bending or shaping patient-specific orthodontic archwires, retainers, or other orthodontic or medical devices to a configuration having a desired geometry.

B. Description of Related Art

In orthodontics, a patient suffering from a malocclusion is treated by affixing brackets to the surface of the teeth and installing an archwire in the slots of the brackets. The archwire and brackets are designed to generate a customized force system that applies forces to teeth, by which individual teeth are moved relative to surrounding anatomical structures into a desired occlusion. The most common approach to creating such a force system is to use off-the-shelf brackets, with or without built-in standardized prescription values, and designing a customized archwire that has complex bends designed to move or rotate the teeth in the desired direction.

These complex bends are characterized by superposition of rotation along the length axis, change in angles in two planes orthogonal to the length axis, and displacements in the length axis and transverse to the wire. In general, these deformations are described by six degrees of freedom. In orthodontics, the change in angles are specified as torque, rotation and angulation. The displacements are specified according their direction relative to the teeth geometry as mesial-distal, buccal-lingual and occlusal-gingival.

The wire segment to be deformed is smaller than the distance between the nearest edges of the bracket slots of the brackets bonded to two adjacent teeth and is usually in the range of only a few millimeters.

Machines for bending orthodontic archwires have been proposed in the prior art. Andreiko et al., in U.S. Pat. No. 5,447,432, describes an apparatus that takes a straight archwire and imparts a simple planar arcuate curvature to the wire. The wire is customized in the sense that the shape of the arc is designed for a particular patient, but the wire bending apparatus described in Andreiko et al. is limited to a customized bracket approach to orthodontics. In particular, the Andreiko et al. wire bending apparatus cannot produce any complex bends in the wire, e.g., bends requiring a combination of translation and rotational motion. The required force system is created by virtue of the design of customized brackets, and in particular slot positions and orientations in the brackets and their exact placement on the teeth in desired positions, such that the brackets interact with the flat planar wire to move teeth into desired positions.

The patent to Orthuber et al., U.S. Pat. No. 4,656,860, describes a bending robot for bending archwires. A robot as described in the '860 patent was developed by the predecessor of the assignee of the present invention and used experimentally for several years, but never widely commercialized. The robot consisted of two characteristic design features: a bending cone that could move forwards and backwards to bend the wire, and a rotating cone that could twist the wire. Accordingly, this machine could perform, within a single bending step, only a deformation around a main axis of the wire. To do a complex deformation of the archwires with six degrees of freedom as commonly required for orthodontic patient-specific archwires, the machine of the '860 patent would typically require a sequence of five single bending steps, comprising three torque (twisting) steps and two bending steps. The archwire segment length necessary to accomplish these plurality of steps usually exceeds the available distance between the nearest edges of the two adjoining bracket slots. Hence, the '860 patent would not work for many orthodontic prescriptions. Additionally, the '860 bending machine was rather imprecise because the robot has no effective feedback mechanism for detecting how the wire in fact was bent after a particular bending or twisting operation was performed. Furthermore, manufacturing inaccuracies of each bending step lead to a relative large error in the whole deformation between two adjacent bracket slots.

The deficiencies in the '860 patent led the present assignee to develop an improved wire bending machine, described in the patents of Werner Butscher, et al., see U.S. Pat. Nos. 6,612,143; 6,732,558; 6,755,064; 6,860,132; 7,076,980 and 7,283,891. The entire content of these patents is incorporated by reference herein. These patents describe an articulated robot arm with six consecutively arranged rotation axes capable of movement in six degrees of freedom to bend an orthodontic wire. To perform the wire deformation, the wire is gripped by both a fixed gripping tool mounted to a table or base, and by a gripping tool mounted at the end of a robot arm. By appropriately moving the robot arm, the segment of the wire gripped between the two grippers is bent and/or twisted to a desired deformation. A variety of other configurations for the robot arm were proposed, including one based on a combination of translation and rotational axes (see FIG. 9 of the '143 patent).

The assignee's work related to wire bending machines as described in the above-referenced U.S. Pat. Nos. 6,612,143; 6,732,558; 6,755,064; 6,860,132; 7,076,980 and 7,283,891 has resulted in the inventors' appreciation that the robot described in these patents, while representing a substantial advance in the art, nevertheless has several shortcomings.

Firstly, the geometry of the bends that can be manufactured is limited and does not allow for creation of all the wire shapes desired by orthodontists. In cases where the bend length must be very short, such as in lingual cases, the treatment options can be limited by this approach.

Secondly, highly accurate archwires are difficult to obtain in a repeatable manner by the robot described in these patents. To guarantee the desired accuracy of finished archwires, the archwires must be measured after the bending has been completed. If the deviations between actual and desired shapes exceed tolerance limits, the wire must be re-bent (i.e., a new wire created). Bending correction values are calculated from errors measured during the first manufacturing run, and are used during the second iteration to obtain a more accurate archwire. A third iteration could also be required in order to fulfill the tolerance limits at all bends of a certain archwire. This process wastes wires, increases production time, and increases manufacturing costs.

The present invention provides a machine for bending medical devices such as orthodontic archwires, and a method of bending such devices, that overcomes these shortcomings, thereby providing a further substantial advance of the prior art. The machines and methods of this invention enable the bending of orthodontic archwires with significantly improved precision with much wider range of possible shapes, and while lowering manufacturing costs.

SUMMARY

In a first aspect, a machine is described below that enables precise bending of an elongate, bendable medical device such as an orthodontic archwire from an initial shape into a desired new shape. The machine includes at least three revolute joints defining controlled rotation axes arranged relatively to each other in such a way that none of the rotation axes are parallel and the rotation axes do not lie in one plane. In preferred implementations, the revolute joints are arranged in mutually orthogonal axes but this is not absolutely necessary. The machine further includes at least three prismatic joints defining controlled translation axes arranged relatively to each other in such a way that the translation axes are not parallel to each other and the translation axes do not lie in one plane. Again, in preferred implementations, the prismatic joints are arranged in mutually orthogonal axes but this is not absolutely necessary.

The at least three revolute joints and at least three prismatic joints are combined in any fashion or sequence into a compact bending apparatus comprising a first compact, moveable manipulator and a second separate, compact, moveable manipulator. The manner in which the three prismatic joints and three revolute joints can be combined into first and second manipulators can take several forms. In one form, the first manipulator includes the three prismatic joints and one revolute joint and the second manipulator includes the remaining two revolute joints. Other possible configurations are described below.

The machine further includes a first gripping tool affixed to the first manipulator and a second gripping tool affixed to the second manipulator. Each of the gripping tools have a gripping structure (e.g., opposed gripping fingers or collet) for releasably holding the medical device. The first and second manipulators are arranged in such away that the first and second gripping tools are able to move relative to each other in six degrees of freedom.

The machine further includes a control unit operable of the first and second manipulators and the first and second gripping tools so as to form a bend in the medical device.

In another aspect of this invention, a method of bending a medical device is disclosed, comprising providing a compact bending machine in the form of a first compact, moveable manipulator and a second separate, compact, moveable manipulator. The bending machine further includes a first gripping tool affixed to the first manipulator and a second gripping tool affixed to the second manipulator. Each of the gripping tools has a gripping structure for releasably holding the medical device. The first and second manipulators are constructed and arranged in such a way that the first and second gripping tools are able to move relative to each other in six degrees of freedom. The method further comprises the steps of gripping the medical device by the first and second gripping tools, and precisely controlling the movement of the first and second gripping tools and the first and second manipulators so as to form a bend and/or twist in the medical device.

In operation, to place the desired deformation in the medical device, the medical device (e.g., orthodontic archwire) is gripped with both gripping tools. The control unit creates input signals for the driving axes of the first and second manipulators in order to generate a relative movement of the two. The medical device stays in a firmly gripped condition by the two gripping tools. Due to the relative movement between the two grippers, the medical devices experiences a deformation into the new desired geometry.

A third or more gripping tool affixed to a third or more manipulator may be included in addition to allow for bending of wire shapes that cannot be bent with the first and second gripper as described above. In one possible configuration, the third gripping tool is affixed to a manipulator in the form of a handling robot.

The bending machine of this disclosure is suitable for bending not only orthodontic archwires, but also other medical devices with an elongated shape as well, such as prostheses, spinal rods, orthopedic devices such as bone fixation devices, stents, implants, fixation plates, spectacle frames and surgical devices including, e.g., a reamer for root canals.

BRIEF DESCRIPTION OF THE DRAWINGS

In FIG. 1, the appliance center receives a data file in the form of a prescription dictating the shape of an medical device to be bent at the center over a computer network from a remote workstation.

DETAILED DESCRIPTION

Overview

Figure 1:
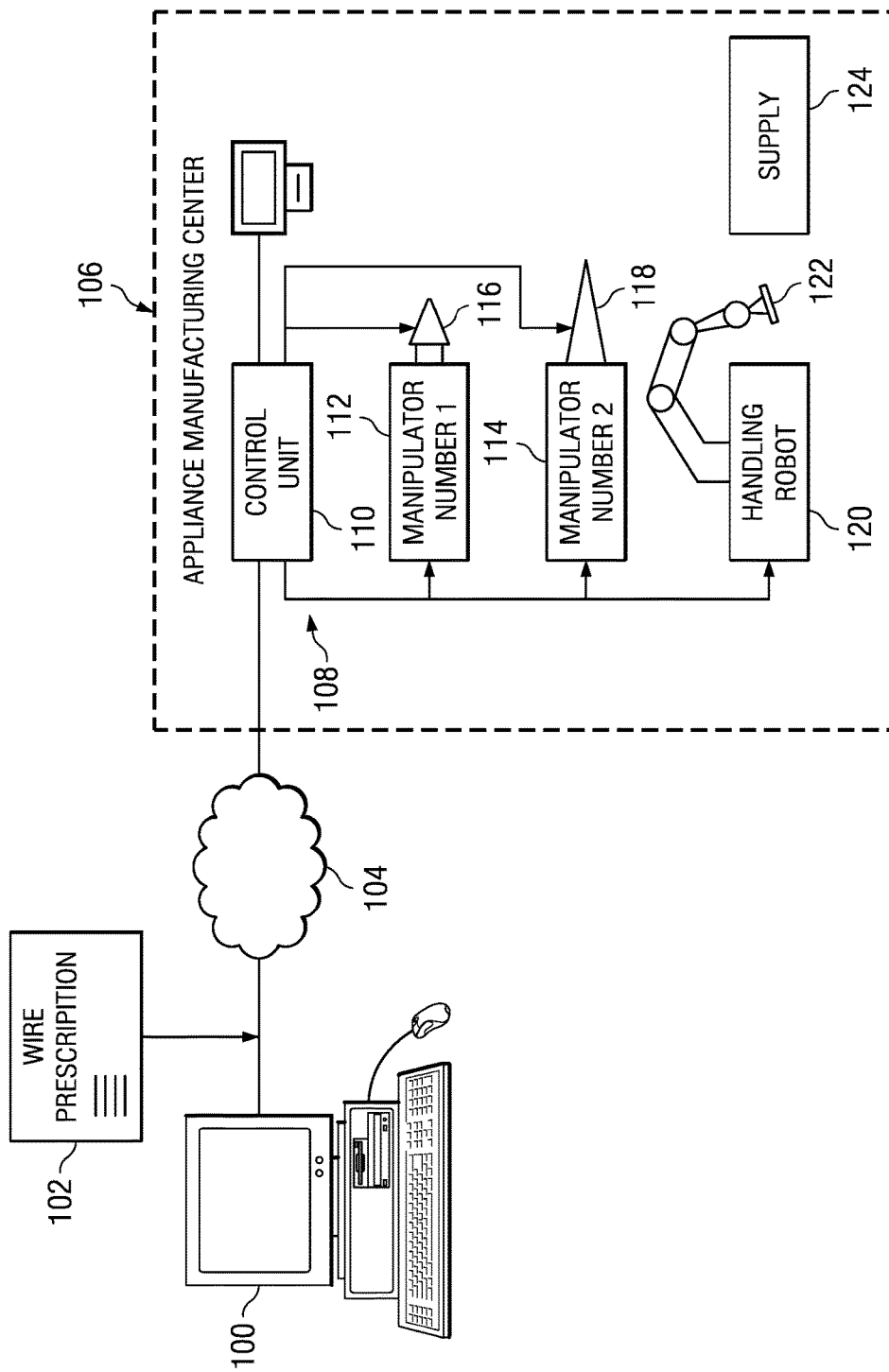
FIG. 1 is a block diagram of an appliance manufacturing center for bending medical devices which includes the bending machine of this disclosure.

FIG. 1 is a block diagram of an environment in which the invention can be practiced. A workstation 100 in the form of a general purpose computer includes interactive orthodontic treatment planning software which designs an orthodontic appliance system for treating a patient. The software operates on a three-dimensional computer model of the patient's teeth in a maloccluded condition. The appliance system includes a customized archwire. The shape of the archwire is dictated by the positions of orthodontic brackets placed on the patient's teeth and the position of the teeth in the target situation. This shape is referred to as an archwire prescription. A datagram 102 containing the archwire prescription is transmitted over a computer network 104 to a precision appliance manufacturing center 106.

The center 106 includes a bending machine 108 for bending an archwire into a desired shape in accordance with the archwire prescription. The bending machine 108 includes a control unit 110, a first manipulator 112, a second manipulator 114, a first gripping tool 116 mounted to the end of the first manipulator 112, and a second gripping tool 118 mounted to the end of the second manipulator 114. Optionally, the bending machine includes a handling robot 120 which obtains an archwire 122 from a supply 124 of archwires and delivers the archwire 122 to one of the gripping tools 116 or 118.

The bending machine 108 proceeds to bend the archwire 122 into a desired configuration in accordance with the wire prescription. The wire is optionally marked, e.g. by a laser, with a legend "left", "right", "upper", "lower", patient name or order number, etc. to assist in identifying the wire and placement of the archwire. The wire is then packaged and shipped to the orthodontist.

Interactive treatment planning software and methods for generating an archwire prescription from a three-dimensional model of a malocclusion are described in the patent literature, see OraMetrix U.S. Pat. Nos. 6,632,089 and 6,648,640, the content of which is incorporated by reference. Therefore, a more detailed description of these aspects is omitted for the sake of brevity.

Compact Manipulators 112 and 114

Figure 2:
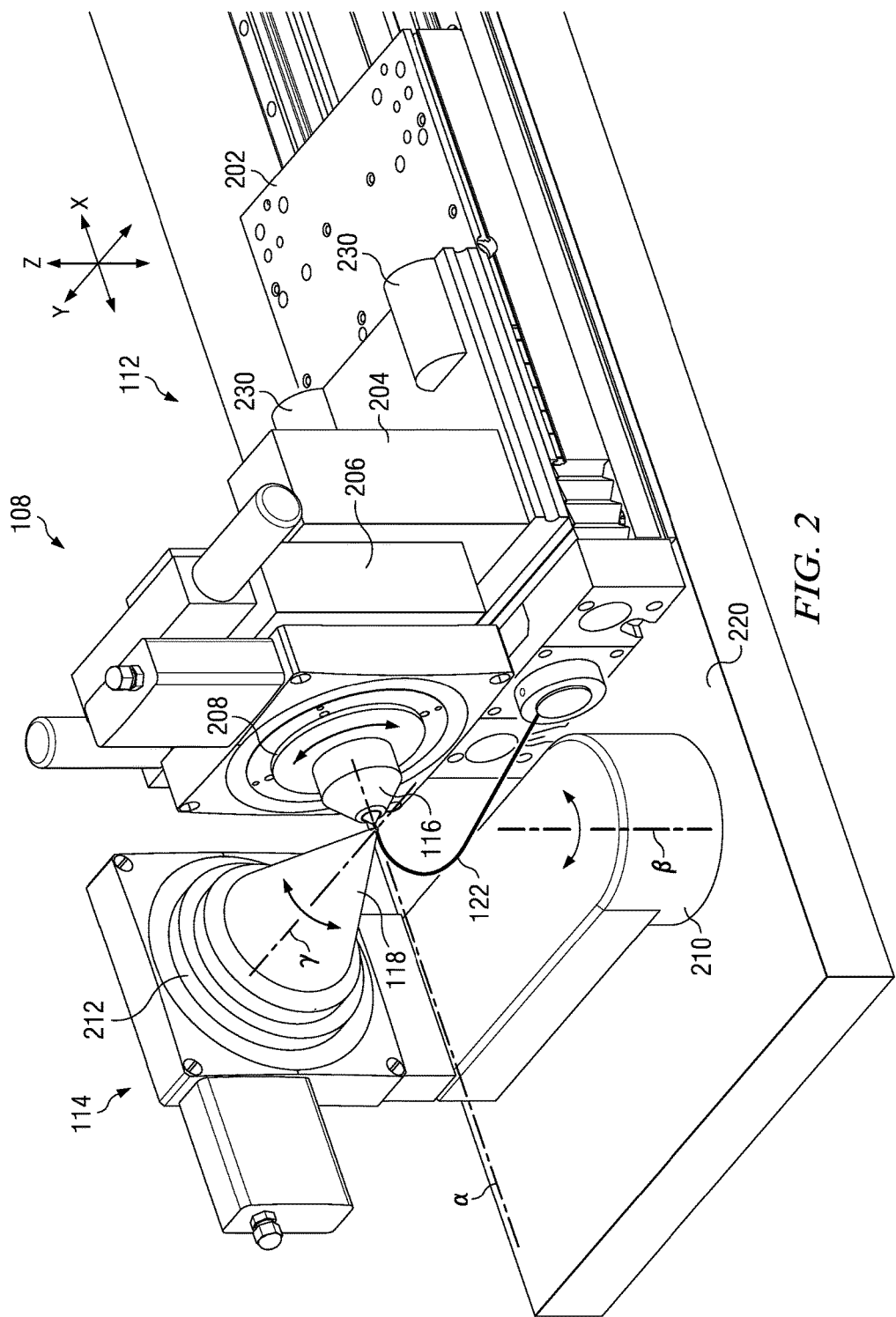
FIG. 2 is a perspective view of the bending machine of FIG. 1, showing two compact manipulators. Gripping tools are mounted to the ends of the manipulators. By virtue of the revolute and prismatic joints making up the manipulators, the gripping tools are moveable relative to each other in six degrees of freedom.

The bending machine 108 of FIG. 1 is shown in greater detail in FIG. 2. The bending machine 108 is based on least three revolute joints defining controlled rotation axes arranged relatively to each other in such a way that none of the rotation axes are parallel and the rotation axes do not lie in one plane; and at least three prismatic joints defining controlled translation axes arranged relatively to each other in such a way that the translation axes are not parallel to each other and the translation axes do not lie in one plane. Furthermore, the at least three revolute joints and at least three prismatic joints are combined in any fashion or combination into a compact bending apparatus comprising a first compact, moveable manipulator 112 and a second separate, compact, moveable manipulator 114.

The manner in which the revolute joints and prismatic joints are combined and arranged into two compact and separate manipulators 112 and 114 may vary. In preferred embodiments, the revolute joints define three mutually orthogonal rotation axes and the prismatic joints define three linear, mutually orthogonal translation axes. In FIG. 2, the first manipulator 112 includes three prismatic joints 202, 204 and 206 and is moveable along the three translation axes X, Y and Z, respectively and includes one revolute joint 208 which is rotatable about axis $\alpha$. In FIG. 2, the second manipulator 114 includes two revolute joints 210 and 212 and is moveable about two rotation axes $\beta$ and $\gamma$.

Figure 3:
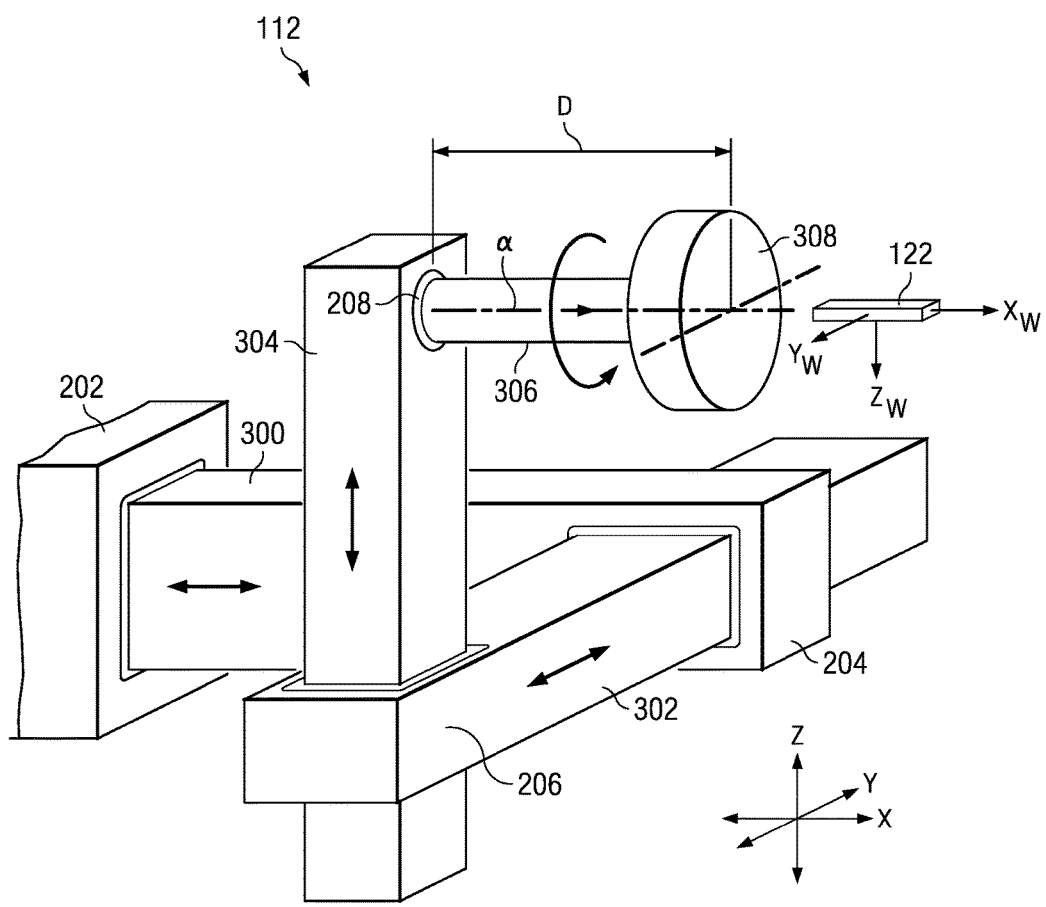
FIG. 3 is a schematic illustration of the joints of the first manipulator of FIG. 2, showing three mutually orthogonal prismatic joints defining three translation axes and one revolute joint connected to the third prismatic joint defining one rotation axis.

The prismatic joints 202, 204 and 206 and the revolute joint 208 of FIG. 2 are shown schematically in FIG. 3. The prismatic joint 202 includes an actuator (not shown, conventional) to move a linear element 300 back and forth along the X axis. The prismatic joint 204 is placed in the distal end of the element 300 and includes an actuator (not shown, conventional) for moving a second linear element 302 back and forth in the Y direction. The prismatic joint 206 is placed in the distal end of the element 302 and includes an actuator (not shown, conventional) for moving a third linear element 304 back and forth along the Z direction. A revolute joint 208 is formed in the distal end of the element 304 for rotation of a fourth element 306 about the axis $\alpha$. The head 306 of the element 308 provides a mounting location for a first gripping tool (not shown in FIG. 3, see 116 of FIGS. 1 and 2). The distance D between the element 304 and the head 306 is constant.

As shown in FIG. 3, the archwire 122 that is gripped by the first gripping tool 116 is oriented such that the long or longitudinal axis of the wire ($X_w$) is oriented along the rotational axis $\alpha$ of the revolute joint 208. Hence, when the wire is gripped by the second gripping tool 118 and the revolute joint 208 is rotated, the wire is twisted about the wire axis $X_w$. The wire 122 is shown having a rectangular cross-section. This cross-section defines mutually orthogonal wire axes $Y_w$ and $Z_w$.

Figure 4:
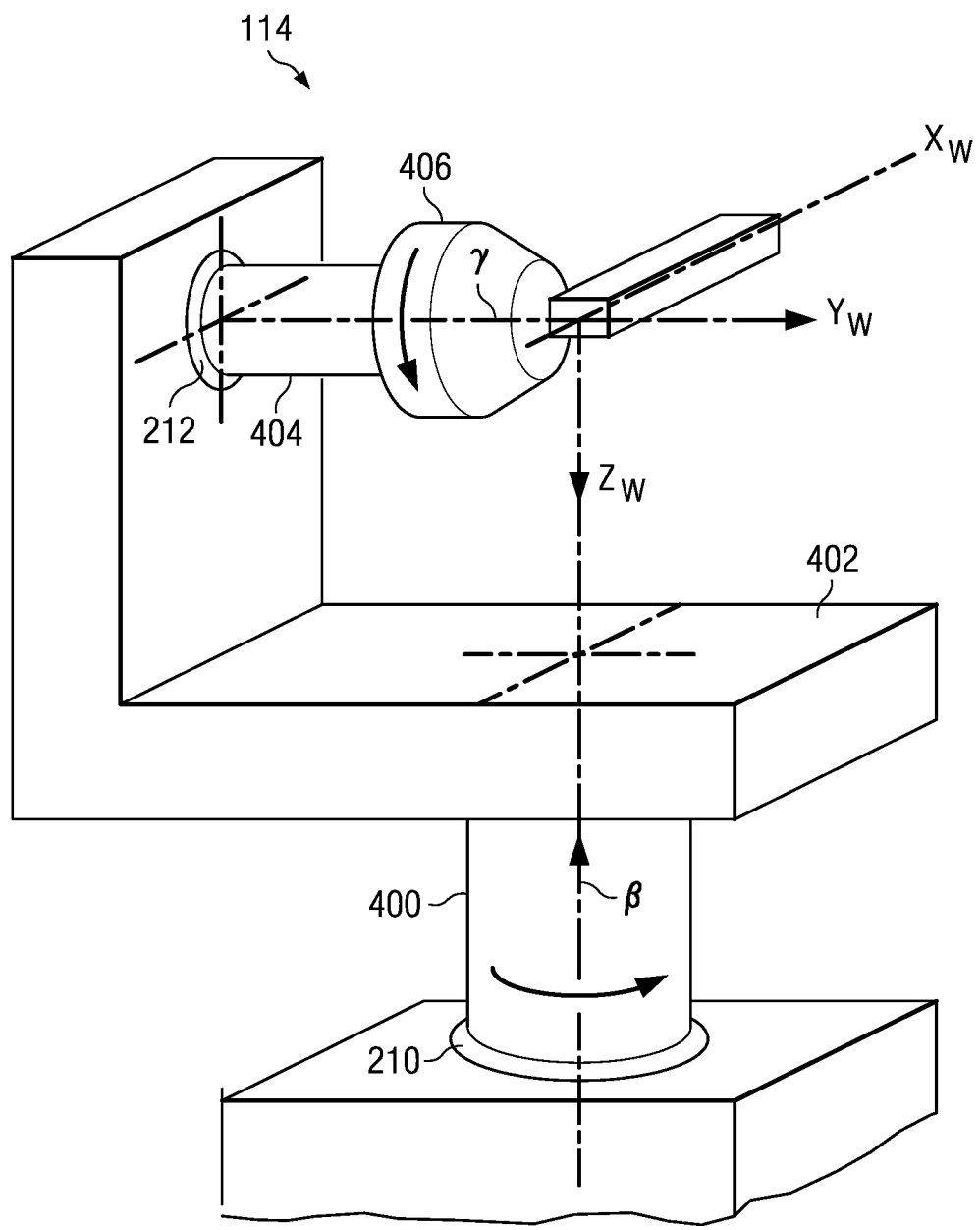
FIG. 4 is a schematic illustration of the joints of the second manipulator of FIG. 2, showing two mutually orthogonal revolute joints.

The second manipulator is shown schematically in FIG. 4. The manipulator 114 includes a first revolute joint 210 which includes an actuator (now shown, conventional) which rotates a first element 400 about the axis $\beta$. A second L-shaped element 402 is connected to element 400, the distal end of which includes a second revolute joint 212 having an actuator (conventional, not shown) which operates to rotate a third element 404 about axis $\gamma$. The head 406 of the element 404 forms a base for mounting the second gripping tool (FIGS. 1 and 2, item 118). The second gripping tool 118 mounted to the end of the second manipulator 114 (FIGS. 1, 2) grips the wire. Movement of the revolute joints 210 and 212 causes the gripping tool to move about axes $\beta$ and $\gamma$. FIG. 4 also shows the wire's orthogonal coordinate system $X_w$, $Y_w$ and $Z_w$.

Referring again to FIGS. 2 and 3, the bending machine 108 is thus designed with a first gripping tool 116 affixed to the first manipulator 112 and a second gripping tool 118 affixed to the second manipulator 114, with each of the gripping tools 116 and 118 having a gripping structure for releasably holding the medical device, e.g., archwire 122. The first and second manipulators 112 and 114 are arranged in such away (due to the combination and arrangement of the revolute and prismatic joints) that the first and second gripping tools 116 and 118 are able to move relative to each other in six degrees of freedom.

The design of FIG. 2 is much more compact than the arrangement of the six axis bending robot of the prior Butscher et al. patents, resulting in a much stiffer and more precisely controllable bending machine. Preferably, the length and range of travel of the of the elements 300, 302, 304, and the length D of FIG. 3, is on the order of a few centimeters or less. Furthermore, the length of the elements 400 and 406 and the legs of the L shaped element 402 of FIG. 4 are in the order of a few centimeters or less.

Preferably, in the situation where the medical device (e.g., archwire) has a rectangular or quadratic cross-section, the translational axis X, Y and Z are aligned according to the principle axes $X_w$, $Y_w$ and $Z_w$ of the wire 122 gripped by the respective gripping tool 116.

In the preferred embodiment the rotation axis α of the first manipulator 112 is aligned according to the wire length axis $X_w$ of the wire segment gripped by the gripping tool 116 on the first manipulator 112 (see FIGS. 2 and 3). In this case, rotations around the axis α represent a rotation of the wire 122 around its length axis (i.e., producing a twist in the wire). One translation axis (axis X defined by the prismatic joint 202) is also aligned in direction of the wire length axis $X_w$. This translation axis $X_w$ allows movements of the gripped part of the wire along its longitudinal direction. The other two translation axes Y and Z defined by the prismatic joints 204 and 206 of the first manipulator are perpendicular to the translation axis X and form an orthogonal system. Preferably, the directions of the axes Y and Z are defined according to the principle axes $Y_w$ and $Z_w$ of the wire segment gripped by first gripping tool 116.

The rotation axes β and γ of the second manipulator 114 are arranged in a way that they correspond to the principal axes $Y_w$ and $Z_w$ of the wire segment gripped by second gripping tool 118 as shown in FIG. 4.

To place the desired deformation, the wire 122 is gripped with both gripping tools 116 and 118. The control unit 110 (FIG. 1) creates input signals for the driving axes of the prismatic and revolute joints in order to generate a relative movement of the two manipulators 112 and 114. The wire 122 stays in a firmly gripped condition by the two gripping tools 116 and 118. Due to the relative movement of the gripping tools 116 and 118, the wire segment between the two gripping tools experiences a deformation into the new desired geometry.

A bending apparatus designed and constructed according to the present disclosure avoids all the drawbacks of the prior art. In particular, the arrangement of a bending machine 108 into a compact design as shown in FIG. 2 with individual, separate compact manipulators 112 and 114 having associated gripping tools 116 and 118 overcomes many of the problems discovered with the multi-axis bending robot described in the prior patents of Butcher et al.

In particular, the inventors discovered that the multi-axis robot arm due to its typical kinematic layout (consecutively arranged 6 rotational axes) requires extremely large movements in space to effect the functionally needed small movements at the tip of the gripping tool. A rotation of the gripper around the longitudinal axes of the wire to be bent in many cases requires for the desired change of the position of the gripper tool relatively to the wire of only parts of a millimeter movements of the robot joints or arms that are larger by a factor of 500 and more, thus reducing the achievable accuracy significantly. For that reason, a volume of the robot workspace well over 1 meter in each of three directions is required. The required large changes in joint angles to correctly position in the moveable gripper with respect to the fixed gripper lead in addition to many restrictions, e.g., the maximum allowed turning angles of the joints could be exceeded. The target configuration may be unreachable without collisions between components of the robot or between the robot and other parts of the work cell housing the robot. The cabling and hoses required for the moveable gripper may become tangled, stretched or damaged. In total, this limited range of motion restricts the desired bending shapes to the ones that can be manufactured, rather than the ones the orthodontist would prefer to use. The compact arrangement of the bending machine as shown in FIG. 2 overcomes these problems and allows the wires to be bent in any desired configuration.

Additionally, the multi-axis robot arm described in the prior patents of Butscher et al. were designed and are typically used for fast, complex and high precision assembly or handling of parts typically in an industrial environment such as wafer handling, assembly of injection pumps, varnishing in the automotive industry, and application of glue and coating in the optical industry. A main focus for their development was to allow very fast movements and be very precise regarding the reproducibility when moving repeatedly to the same location (approximately 0.02 mm) or with the same pattern of movements. To get the highest possible accuracy typically the robots are adjusted to optimize their positions and movements for a certain task repeated over and over again.

In contrast, manufacturing of patient specific bends in an orthodontic archwire demands the movement to new positions with quite different joint configurations. This requires an absolute accuracy of the robots, meaning that based on a mathematical model of the robot the absolute position and orientation of the arm in space can be calculated with high accuracy. However, the geometrical and kinematic models of off-the-shelf six axis robot arms are not as exact as desired. Even small deviations of the ideal geometry of the components of the gearboxes, especially discontinuous deviations of the geometry of the gearwheels, lead to reduced accuracy regarding absolute positioning. The typical industrial robot arm is arranged as a serial kinematic chain of gearboxes and "link segments" where each small gearbox error compounds the errors of gearboxes further up the serial chain. It has been found that for typical orthodontic bending shapes, the desired verses actual position error may be as large as 0.5 mm. Several additional measures are required to compensate for this problem. For example, each robot must be measured and calibrated in order to generate an optimized mathematical model of the "real robot", which considers the manufacturing tolerances of the specific machine and offers increased accuracy than the standard model of an "ideal robot" by the manufacturer. This calibration is technically most demanding and rather expensive. Furthermore, testing for changes to the "real robot" model due to wear must be part of an ongoing preventative maintenance schedule. These problems are overcome with the new bending machine described herein and shown in FIG. 2.

Additionally, the stiffness of the robot of the Butscher et al. patents with six consecutively arranged rotation axes is rather low due to its open kinematic structure. This relatively low stiffness limits the accuracy of the bends due to the forces and moments exerted into the robot arm during the bending process. For typical bends, these forces are relatively small (between about 40 Nmm and 1000 Nmm, respectively), but because of the large volume and dimensions of the robot, and therefore a rather large leverage effect, they still cause deformations in reference to the gripper tip (up to 0.4 mm), which are not negligible. In order to guarantee the desired accuracy for orthodontic archwires, additional measures must be defined for compensating for this "softness" of the robot. For instance, the approximate forces and moments during the bending operation can be calculated in advance based on a mechanical model and appropriate movements can be defined to compensate the robot deformation.

A further characteristic of the robots described in the prior Butscher et al. patents is the relatively low effective load they can manipulate. Sharper bends with strong deformations of the wire may require bending forces and moments exceeding the maximum payload of the robot. Therefore, such sharp bends cannot be manufactured. Conversely, with the bending apparatus of this invention such sharp bends with strong deformations can be achieved.

As a result of the new bending machine and method of this disclosure, there are fewer restrictions concerning the forming of complex bends. The movements of a certain axis correspond directly to a deformation of the medical device around or along its principal axes. The maximum allowed range of the displacements and angles of the bending machine permits bending geometries which clearly exceed the clinical needs of the orthodontist. Furthermore, the illegal arm configurations and collision problems that exist in the prior art have been eliminated.

The design of a bending apparatus according to the invention is significantly more compact and stiffer compared to the design based on an arm with six consecutively arranged rotation axes as shown in the Butscher et al. patents. The compliance (i.e., flexibility) of the manipulators 112 and 114 against bending forces and moments is significantly reduced due to their compact arrangement. The desired wire deformation can therefore be made with higher accuracy.

Furthermore, unlike the prior art, the bending machine has a simple structure, which can be realized with high accuracy. And, importantly, the errors are not accumulated and amplified along the serial link-chain configuration as is the case with a single arm having six sequential rotation joints as in the Butscher et al. patents. This bending apparatus can be designed and built based on high quality components in a way that the required absolute accuracy in movement can be achieved without calibration.

Unlike to the bending machine of this disclosure, the movement of a single axis of a standard industrial robot with six consecutively arranged rotation axes cause a very large movement of the wire in space. This movement cannot be monitored with available camera or other measurement systems with sufficient accuracy.

The bending machine of this disclosure also allows for either straight or curved preformed archwires to be used as the raw material. Such preformed archwires with a curved shape are commonly used to close the spaces between teeth, but are not typically custom-made for a specific patient. The ability of this bending apparatus to apply custom bends to preformed archwires will allow space closures to be performed at the same time other tooth movements are applied, thus shortening the required treatment time.

The bending machine of this disclosure is suitable for bending not only orthodontic archwires, but also other medical devices with an elongated shape as well, such as prostheses, orthopedic devices, stents, implants, fixation plates, spectacle frames and surgical devices including a reamer for root canals.

To calibrate the manipulators 112 and 114, a certain axis movement can be carried out and the actual movements of the wire are monitored with a machine vision (camera) system described in more detail below. By comparing the desired movement and the actual movement the precise position and orientation of the driving axis can be determined. Based on the precise positions and orientations for all axes a real model of the bending core can be developed. The necessary movements can then be calculated based on this real model.

Unlike the bending machine of this disclosure, the movement of a single axis of a standard industrial robot with six consecutively arranged rotation axes causes a very large movement of the wire in space. This movement cannot be monitored with available camera systems with sufficient accuracy.

Control Unit 110 (FIG. 1)

The control unit 110 is a general purpose computer with an extension board to control the prismatic and revolute joint axes drives. Such extension boards are for example available from Beckhoff Automation LLC, Burnsville, Minn. 55337, USA. Additional interfaces such as CANbus or Ethernet-interface allow the communication with a gripper heating controller and a wire heating controller (both not shown). The design of the control unit follows the general outlines of the robot controller and related control system shown in the Butscher et al. U.S. Pat. No. 6,612,143, (see FIGS. 2 and 2A of the '143 patent and the related description thereof), the content of which is incorporated by reference herein. The implementation of a control unit for the bending machine of FIG. 2 can be accomplished by persons skilled in the art from the present description and the teachings of the '143 patent.

In operation, the control unit generates commands for the prismatic and revolute joint axes drives of FIGS. 3 and 4 and the gripping tools 116 and 118 of FIGS. 1 and 2) to move the joints the desired amount and open and close the gripping tools to grip and release the wire, and advance the wire to a new position for placement of a successive bend and/or twist in the wire.

Gripping Tools 116 and 118

The first and second manipulators 112 and 114 each include a gripping tool shown as 116 and 118 in FIG. 2. The gripping tools can take several forms. In one form, one of the gripping tools takes the form of the gripping tool 118 shown in FIG. 6 in the form of a gripper 600 having includes a pair of opposed gripping fingers 602 and 604.

The other of the gripping tools 116 takes the form of a collet 700 (FIG. 7) having elements 700A, 700B, 700C and 700D which retract and extend from a base 702 to grip or release the archwire 122. Alternatively, both the gripping tools 118 and 116 could take the form of a collet or opposed gripping fingers. Still other variations and designs for the gripping tools are possible.

Figure 6:
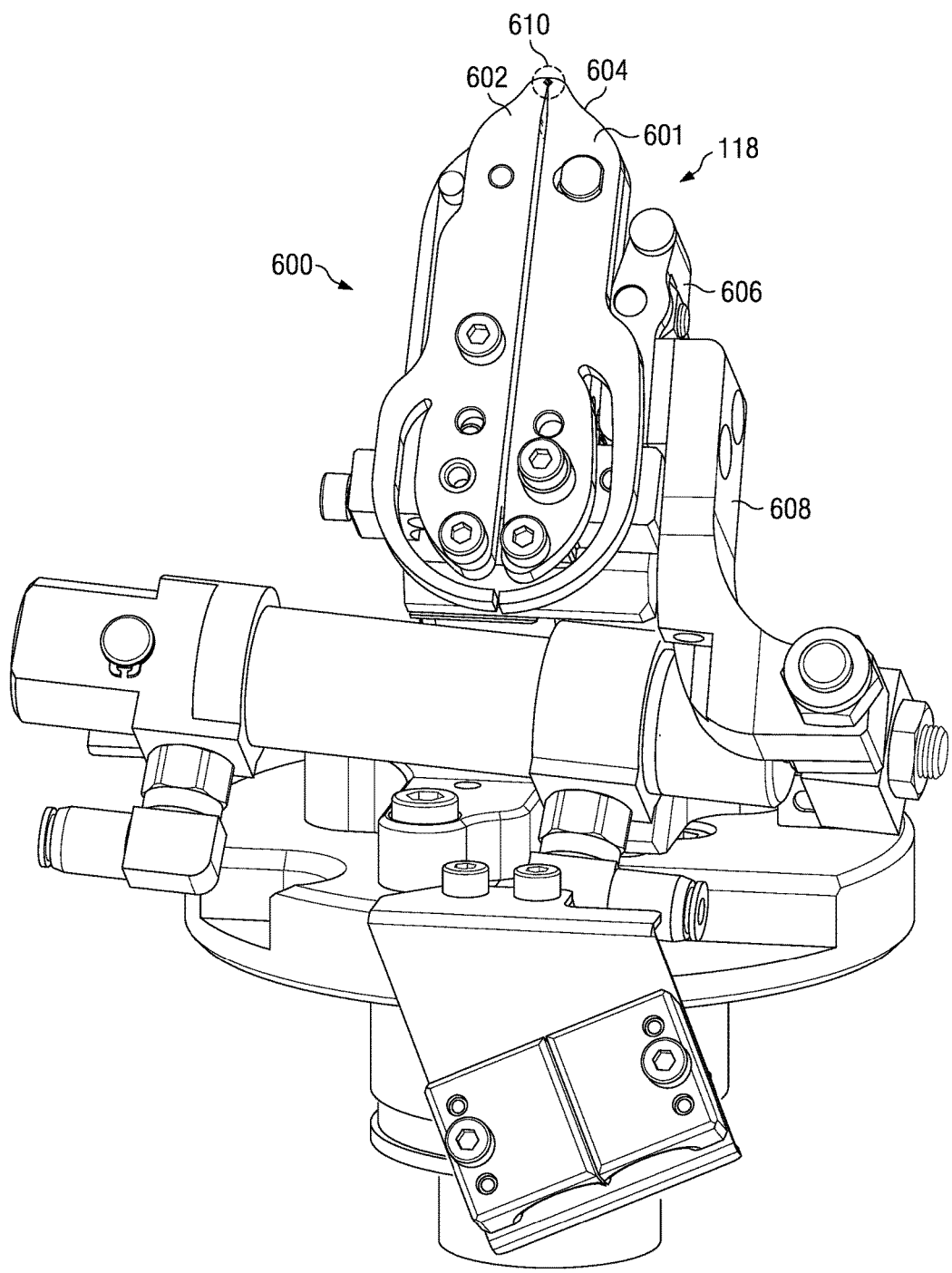
FIG. 6 is a perspective view of a preferred gripping tool in the form of two opposed gripping fingers.

The collet design (FIG. 7) allows higher gripping forces and a better accuracy of the gripping position than the design with two opposing gripping fingers (FIG. 6). However, the collet type of gripper is not capable of complete release and departure movements from the wire. The preferred wire bending process requires at least one of the gripping tools to have the ability to release, depart from and re-grip the wire, hence at least one of the tools is preferably in the form of gripping fingers (FIG. 6) since this capability is achievable with gripping fingers.

FIGS. 5A-5D shows different gripping contours in the gripping fingers 602 and 604 to grip triangular, rectangular and round cross-sections of a medical device, e.g., archwire 122. The gripping contours could also be provided in the elements 700A, 700B, 700C and 700D of the collet 700. Preferably, the gripping tool 118 of FIG. 6 is realized as two opposing gripper fingers 602, 604, which have a contour in the region 610 (FIG. 6) to grip the wire, e.g., as shown in FIG. 5A-5D. At least one finger 602 or 604 is pivoted and can be moved, for example, by a pneumatic actuator 606. Sensors 608 are mounted to indicate the opening and closing position of the gripper. By closing the gripper, the wire 122 gets fixed in a predefined position and orientation in the gripper. The maximum opening width should be big enough to allow a complete release and departure of the gripper from the wire.

Referring to FIG. 6, the gripping fingers 602 and 604 can be integrated in a kind of insert (gripping plate 601). Eventually, the gripping contour in region 610 will wear due to friction against the wire. In this case, the gripping plate 601 can easily be exchanged for a new one. The gripper plates 601 can be equipped with several contours to grip wires in the region 610. Each of these contours is adjusted to grip a certain wire cross-section. The most common cross-sectional configurations are square, rectangular and round cross-sections. However, addition cross-sections include triangular, polygonal, oval, elliptical or profiled (i.e. like a gearwheel) cross-sections. By having multi-contour grippers, the bending apparatus can produce wires of different cross-sections (see FIGS. 5A-5D) one after the other without the need for changing the grippers. This makes the manufacturing more flexible in response for the customer wishes concerning wire cross-section.

It will be further noted that different types of medical devices may have different shapes and thickness than the archwire examples, and the design of the gripping tools modified as necessary to accommodate such different types of medical devices.

Figure 5A:
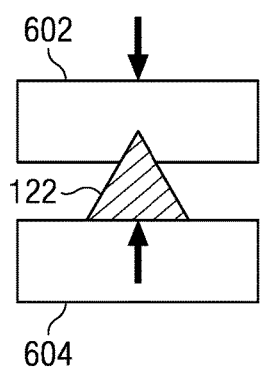
FIG. 5A-5D are illustrations of gripping contours formed in the gripping tools so as to grip medical devices having triangular, rectangular and round cross-sections.
Figure 5B:
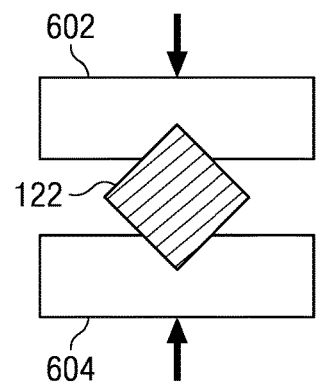
Figure 5C:
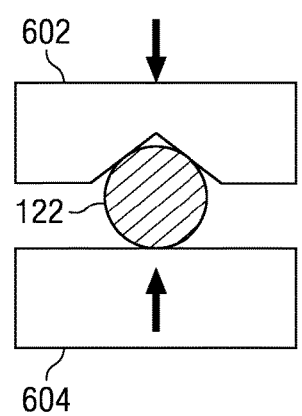
Figure 5D:
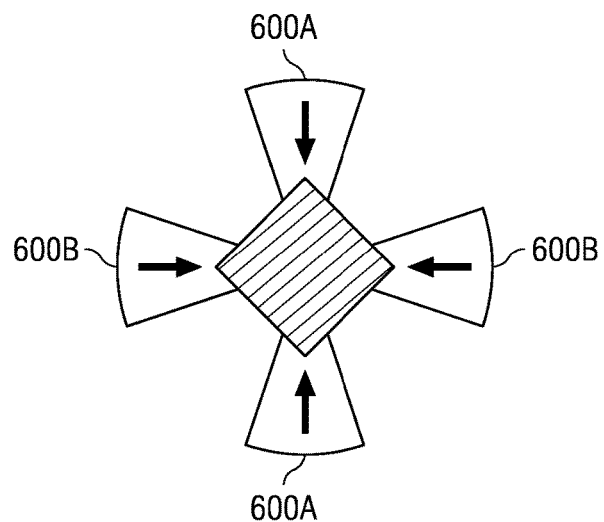

The gripping contour in the region 610 is adapted to the wire cross-section as shown in FIGS. 5A-5D. Different shapes may be chosen depending on the shape of the cross-section. FIGS. 5A-5D shows shapes for the gripping fingers to grip wires with different cross-sections such as triangular (FIG. 5A), rectangular/square (FIGS. 5B and 5D), and round or oval (FIG. 5C). FIG. 5D also shows configuration where two gripping tools 600A and 600B, each with two fingers, are holding a wire with a square or rectangular cross-section. One skilled in the art would appreciate that other contours adapted to a variety of different cross-section shapes like trapezoid, pentagonal, hexagonal are possible.

In another aspect the gripping tools 116 and 118 are equipped with an actuator which supports a controllable opening movement. This can be realized by using an electro-mechanical actuator. Such a design allows a partial opening of the gripping tools for example to let the wire slip through the gripping tools in case of too high bending forces, or in order to reposition the gripper along the wire without losing contact between wire and gripper during the movement.

Figure 9A:
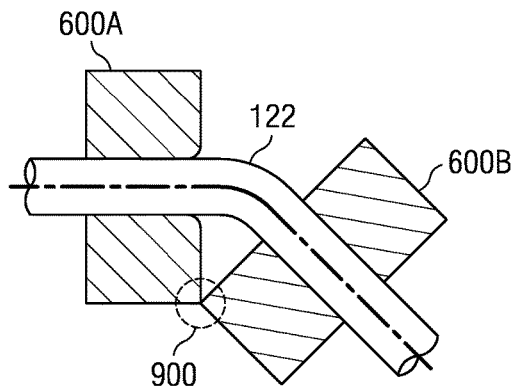
FIG. 9a is an illustration of a scenario in which a collision between two grippers occurs while bending a wire.

Gripper fingers (FIG. 6) according to the above described design enclose the wire completely in the gripped situation. However, the necessary thickness of the gripper fingers 602 and 604 limits the range of possible bending positions. Bending positions with a very short grip distance and a large change in orientation may cause a gripper collision. This is illustrated in FIG. 9A where grippers 600A and 600B are holding archwire 122, and in the process of bending the archwire collide as indicated at 900. Although such extreme bends may be required for orthodontic treatment only rarely, a method to broaden the bending capabilities of the disclosed bending apparatus even for such bends is given below.

Figure 9B:
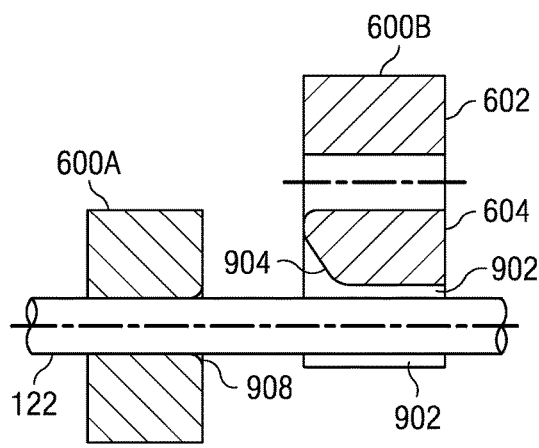
FIGS. 9b and 9c illustrate a gripping tool with a bending contour at its outer edge, showing its use in avoidance of collision between two gripping tools while bending a wire.
Figure 9C:
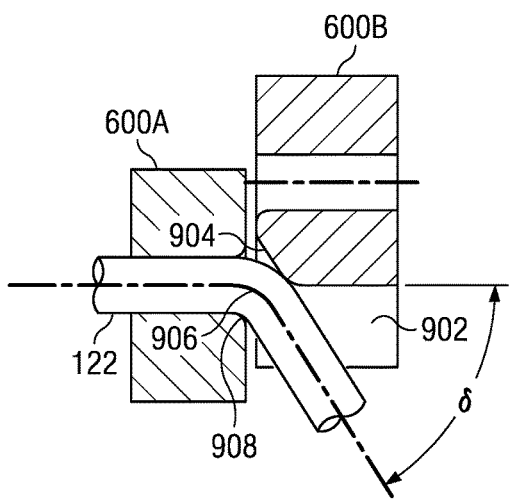

FIG. 9B illustrates a configuration where gripping tools 600A and 600B are used to bend a wire 122. The gripping tool 600B has, in addition to the desired gripping contour (FIG. 5A-5D), a bending contour 904 at the outside edge of one of the gripping fingers 604. This bending contour 904 further includes a groove 902 on the outside edge of the finger 604 to guide the wire 122 during forming and bending the wire into a shape with smooth radii of curvature in order to provide a steady deformation of the wire 122 without forming cracks or other defects in the wire. As shown in FIG. 9C, in order to perform the shaping process, the wire 122 is gripped by the gripper 600A. The gripper 600B with the bending contour 902 acts in the manner of a bending punch. At first, the wire 122 is inserted into the groove 902 by correspondent movements of grippers 600A and 600B. Next, movements of grippers 600A and 600B are made in such a way as to place the wire 122 into the bending contour 904.

The strain on the wire 122 in the bent area 906 (FIG. 9C) can be impacted by varying the distance between bending punch (contour 904) and the bending edge 908 as shown in FIG. 9C. This allows control of the achieved geometry of the bend to a certain extent and helps achieve extremely sharp bends (indicated by angle δ) on short distances.

The bending edge 908 can be designed in a way that the shape is not building a 90 degree edge on both sides of the bending radius but rather a smaller angle. If for example the angle δ is only 70 degrees this allows the wire to be over-bent more than 90 degree thereby achieving even 90 degree angles.

If, in addition, the direction of the movement of the bending punch (gripper 600B in FIG. 9C) relative to the longitudinal axes of the wire to be bent is not perpendicular) (90° but angled, e.g. 110°, bends with angles δ of significantly more than 90° can be achieved. Achieving a maximum flexibility of the both the distance between the bending edge 908 and bending punch (contour 904 of gripping tool 600B) and the angle of the movement of both the bending edge 908 and bending punch 904 can be varied using actuators and measurement systems.

Figure 8:
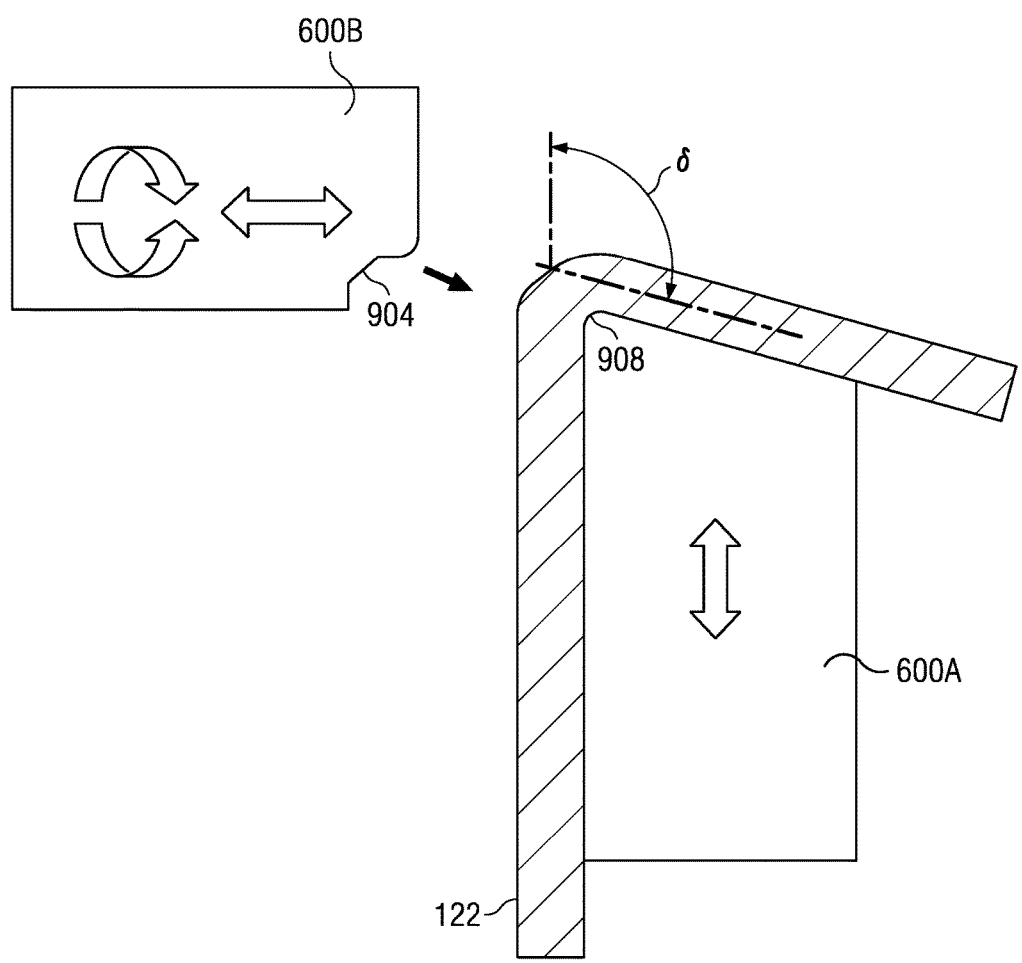
FIG. 8 is an illustration of a bending process using a gripping tool with a bending punch/edge.

FIG. 8 is another view showing an arrangement of gripping tools in the form of grippers 600A and 600B in which gripper 600A includes a bending edge 908 on the peripheral edge thereof and gripper 600 includes a bending punch contour 904. The gripper 600B moves relative to the gripper 600B to bend the wire 122 over the edge 908 and form a bend with a bending angle δ of greater than 90 degrees.

Wire Heating

Depending on the type of wire material to be bent, the bending process may require a heat treatment step. The bending machine 108 is therefore equipped with a wire heating device, which is not shown in FIG. 1, to heat up the wire segment gripped between the two gripping tools.

For some applications, such as bending shape memory alloys, the wire heating device must be able to heat-treat the wire to temperatures up to 700° C. for up to some seconds. The heating is possible by conductive resistance heating, laser, convection or radiation. In the preferred realization, the wire heating device consists of a wire heating controller, which controls a wire heating power supply that supplies a current through the gripping tools and the gripped wire part. The current produces a resistive heating in the wire. The current is controlled via a wire heating current sensor so as to produce a wire temperature as specified. A wire temperature sensor (infrared sensor, pyrometer) or a thermo-camera-system is adjusted to measure the effective wire temperature and therefore to control the wire heating process.

Because the wire 122 has relative low mass in comparison to the gripping tools 116 and 118, the gripping tools may act as a significant heat sink thereby causing the heat loss. To reduce the heat loss, the bending machine further includes a gripper heating device, also not shown in FIG. 2, to heat up at least the gripper fingers 602 and 604 and the collet 700 (FIG. 7) to temperatures above ambient temperature. Such heating may be accomplished by any convenient means.

Force Sensors

To provide a feedback about the forces and moments during the bending process, force sensors are mounted on the manipulators 112 and 114 between the base of the manipulator (where the manipulators are mounted to the table 220 (FIG. 2)) and the gripping tools 116 and 118. In FIG. 2, the force sensors are shown at 230.

Figure 6A:
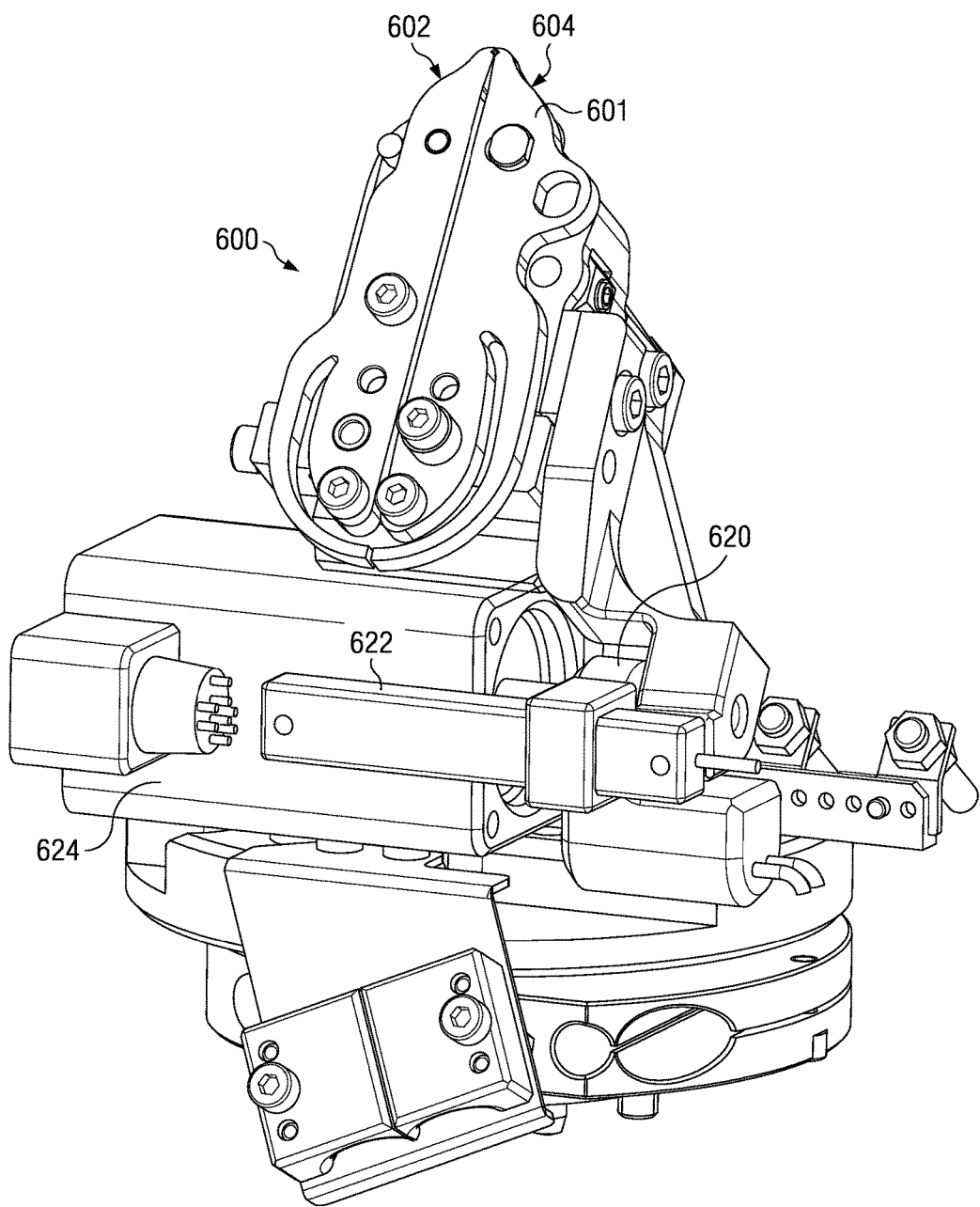
FIG. 6A is a perspective view of another embodiment of the gripping tool of FIG. 6.

For further control and surveillance of the gripping process, a force sensor device can be integrated in the gripping tools 116 and 118. In FIG. 6A, the gripping tool 600 includes a force measurement sensor 620. The force measurement sensor 620 can be implemented by designing a lever so that it gets a measureable deformation during closing the gripping tool and by applying strain gauges on the lever to measure this deformation. Another option is to integrate an off-the-shelf force sensor between plunger of the pneumatic actuator (606, FIG. 6) and the lever. By measuring the relation between the force signal and the gripper closing movement, the correct grip condition can be verified. In the correct grip condition, force signals increase at a certain position or moment in time in the gripping tool closing process, when contact between the wire and gripper fingers occurs. An incorrect grip condition is indicated by a rise of the forces during the gripping tool closing movement that occurs too soon (i.e., earlier than expected), indicating the case of a wrong wire position. If rise of forces occurs too late (i.e. later than expected), it indicates that the wire is missing and has not been gripped at all, indicates that the two gripping fingers come into direct contact.

The forces and moments detected by the force sensors are determined both in magnitude and in direction in three dimensions. The sensor signals are transformed to the grip point (where the wire is gripped by the gripping tool) and into the wire coordinate system as to represent the forces and moments which are acting between the wire and gripping tool.

Because there is a need to detect high and very low forces with good resolution, a sensor with an adjustable measurement range may be used. Alternatively two sensors with a different resolution level can be used. When high forces are acting, only the coarse low resolution sensor with a large measurement range is read, while the fine high resolution sensor is typically in an overloaded condition and is not read. Conversely, when the forces measured by the low resolution sensor indicate that the load is within the measurement range of the high resolution sensor, then the signals of the high resolution are evaluated in order to provide a better resolution of the measurement signals.

The force measurement sensors may be used to provide for measurements to determine the zero force position of the wire after a bending step has been completed. Such measurements may also be used in conjunction with overbending steps as disclosed in the prior patents of Butcher et al. cited previously.

The use of force sensors, e.g., strain gauges, in the bending machine, either on the gripping tools or elsewhere, can be used in a feedback loop to control the operation of the gripping tools and the movement of the gripping tools to move the move the medical device to the desired location.

Still referring to FIG. 6A, the gripper 600 includes a travel measurement system or sensor to measure the movement of the gripper fingers 602 and 604 and a linear servo drive 624 for opening and closing the gripper fingers.

Machine Vision System

After the forming process for a first bend in the wire is completed, the wire must be re-gripped by the gripping tool 118 to continue with the bending process for other bends along the wire. The re-gripping requires that the actual shape of the wire after forming is known very precisely.

Figure 10:
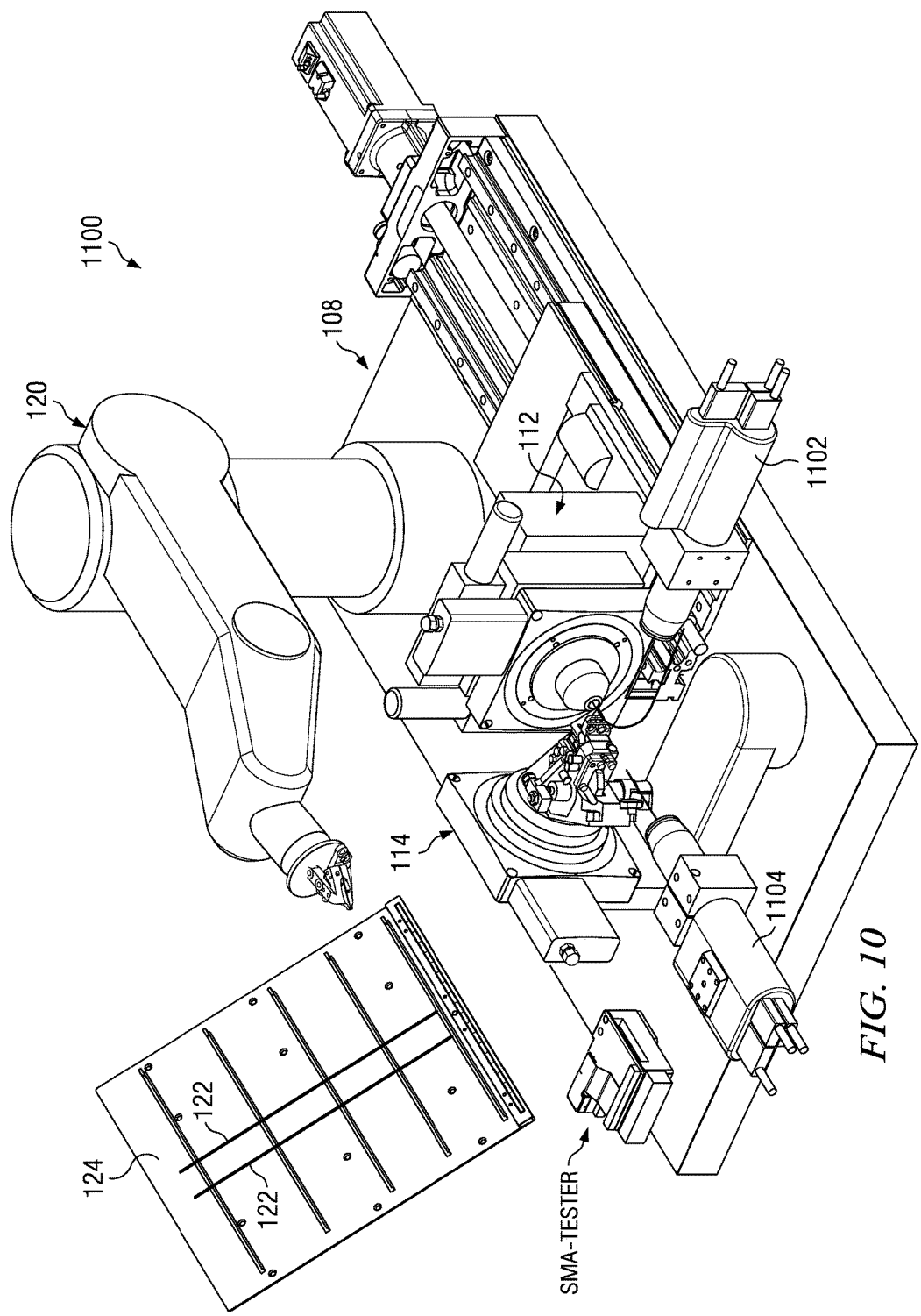
FIG. 10 is an illustration of an industrial wire bending manufacturing cell at the appliance manufacturing facility of FIG. 1, the cell comprising a wire bending machine as shown in FIG. 2, a wire handling robot and a wire storage magazine. Also shown in this figure is a vision system that enables quality control of the bent archwire.

The disclosed embodiment of the bending apparatus includes a machine vision system. As shown in FIG. 10, the machine vision system includes vision components 1102 and 1104 which are positioned proximate to the first and second manipulators so as to detect the actual shape of the bend. The machine vision components 1102 and 1104 can take the form of laser light sources and photodiode detectors. Alternatively or additionally, the machine vision components 1102 and 1104 may also include cameras, including infrared cameras, area scan cameras, line scan cameras, or TDI (time delay and integrate) multi-line cameras, in either CCD (charge-coupled device) or CMOS (complimentary metal oxide semiconductor) configurations.

A machine vision system in the form of a camera system with machine vision software allows the preferred embodiment to both avoid common problems with the prior art, and expands on the ability of the system to make highly accurate bends.

One use of the machine vision system is to grip and re-grip the wire using gripping tool 118 (FIG. 2). Based on the knowledge of the actual shape of the wire measured by the machine vision system, movement commands for the manipulators 112 and 114 can be generated so that the gripping tool 118 approaches the wire at the intended new grip position and re-grips it.

A camera mounted to view the wire along the Y axis of the wire (vision system component 1102 in FIG. 10) is capable of measuring the thickness of the archwire as it is rotated by the axis $\alpha$ (FIG. 2) of the bending apparatus. With this information, it is possible to reconstruct both the actual wire cross section, and the actual bend formed in the wire. If a wide-view lens is used, the completed archwire can be viewed at once, and a digital measurement of the entire archwire can be generated as the wire spins on the manipulator 112 axis $\alpha$. This allows the bending apparatus to perform a quality check on the wire as soon as it is completed. If an archwire fails to meet the specified accuracy, it will be scraped and another archwire can be bent using the bending error measurements from the first iteration as feedback data.

Along with the ability to scan a complete archwire, it is also possible to perform a quality check on the super elastic properties of the SMA (shape memory alloy) wires. Because the bending apparatus can be used to scan the completed archwire by the vision system 1102 and or 1104, it is also able to find and grip the wire on its end with each of the gripping tools mounted to the ends of the first and second manipulators 112 and 114. The manipulators 112 and 114 can then perform a "stretching move" to elongate the wire into an approximate straight line. When the wire is released by the second gripping tool (118, FIG. 2) it will return to its trained shape within a second or two. The wire can then be scanned again (using vision system 1102 and rotation about the axis $\alpha$, FIG. 10 and FIG. 2) to verify that it has returned to the target shape.

The cross-section data collected by the vision system can be used along with bracket information stored in a database to compensate for the clearance tolerances between the wire cross-section and the bracket slot. Wires are bent with the bending machine with extra amounts of torque, angulation and/or rotation to ensure that the wire rigidly interfaces with the bracket in the direction force is to be applied.

The machine vision in this embodiment is also very useful when calibrating the manipulators 112 and 114. Direct measurement of manipulator mechanism parameters, either by direct measurement and tracking of end effectors in the camera's field of view, or by measuring the resultant bends made on special calibration wires is possible.

Part of the calibration problem is to derive the required over-bending values for various alloys. Since the vision system is able to measure single bends as soon as they are made, the correct over-bending values can be automatically found by iteratively bending and measuring bends until the correct over-bending values are found.

In the prior art, the area of the gripper that actually contacted the wire would wear over time. This eventually results in an unreliable grip of the wire. A poor wire grip causes heating to occur between the gripper and the wire, rather than in just the wire segment between the two grippers. This results in a wire that is too soft for effective treatment. The problem is not visible to the operators of the robot manufacturing apparatus, and may not be visible when the accuracy of the bends are measured (e.g. in straight sections of the wire, there will be no change in the resultant wire shape). However, the wire heating described above itself emits a significant amount of infrared light, which can be seen through a camera. Thus, one embodiment of the vision system includes an infrared camera at either vision system component 1102 or 1104. By measuring the intensity of the infrared light along the length of the bend, a heat histogram can be made and this error scenario can be detected. If the ambient light levels are properly controlled, the temperature of the wire can also be derived from the intensity of the light emitted. This insures that the proper temperature for heat treating the wire has been achieved.

In another embodiment, one or more line scan cameras (CCD/CMOS) are used instead of an area scan camera. The entire wire or the area of interest can be scanned by moving it relative to the camera, along the axis of the wire or along other axes, capturing a sequence of linear images and combining the sequence of linear images into a single 2D image or into a multitude of 2D images each from a different perspective. The movement of the wire must be synchronized with the camera exposures.

In another embodiment one or more laser micrometers are used instead of a linear array camera (e.g., in either CCD or CMOS format). The entire wire or the area of interest can be scanned by moving it relative to the camera, along the axis of the wire or along other axes, capturing a sequence of linear images and combining the sequence of linear images into a single 2D image or into a multitude of 2D images each from a different perspective. The movement of the wire must be synchronized with the camera exposures.

In another embodiment one or more TDI multi line cameras are used similar to a line camera. The entire wire or the area of interest can be scanned by moving it relative to the camera, along the axis of the wire or along other axes, capturing a sequence of linear images and combining the sequence of linear images into a single 2D image or into a multitude of 2D images each from a different perspective. The movement of the wire must be synchronized with the camera exposures.

Method of Operation

The method of shaping an orthodontic archwire using the bending machine 108 of FIG. 2 can be summarized as follows. It has to be noted, that the described process does not require a straight shape of the raw material, but rather may use an already curved archwire such as a commonly used preformed planar archwire as well.

The control unit 110 receives an input file that contains the geometrical information about the wire to be manufactured (i.e. wire prescription). The wire is represented as a sequence of straight segments in 3D-space. Between two consecutive straight segments there is a bent segment. The position and orientation of the straight segments towards each other define the shape of the bend to be produced. The control unit 110 calculates the necessary axes movements to achieve the required bending position for each bend. The control unit 110 further controls all the movements in order to reposition the gripping tools along the wire and to form one bend after the other along the wire.

In an initial step, the archwire 122 is inserted into the first gripping tool 116 such that a portion of the archwire projects beyond the first gripping tool 116 in the direction to the second gripping tool 118 (which is referred in the following as projecting to the front) and another portion of the archwire 122 projects in the opposite direction (which is referred in the following as projecting to the back) and then the wire is gripped by the first gripping tool 116.

The insertion process is either performed manually or in case of an industrial environment with high numbers of wires to produce with the aid of a handling robot 120, FIGS. 1, 11. Such an industrial embodiment is described more detailed later on in this specification.

Then a sequence of process steps follows:

1. Moving the first and/or second gripping tools to position the archwire so that it can be gripped by the second gripping tool 118 at the portion of the archwire extending from the front of the first gripping tool 116;

2. Gripping the portion of the archwire 122 extending to the front of the first gripping tool 116 with the second gripping tool 118;

3. Moving the first gripping tool 116 and/or the second gripping tool 118 relatively to each other to deform the wire into the desired shape;

4. Releasing the first gripping tool 116;

5. Moving the first gripping tool 116 and/or the second gripping tool 118 to position the archwire 122 so that it can be gripped by the first gripping tool 116 in the portion of the archwire, which projects to the back of the first gripping tool 116;

6. Releasing the second gripping tool 118;

Steps 1-6 repeat to produce a series of bends and/or twists in the wire according to the wire prescription to thereby produce an archwire of a desired configuration.

When the shaping of the archwire is completed, the archwire may be removed manually from the shaping machine or by an appropriate handling machine like a robot 120 as part of the periphery of the bending machine 108.

Further notes regarding the above process steps:

Step 1 and 5:

The complexity of the movements in step 1 and step 5 depend on the shape of the wire in its initial (undeformed) state and the configuration of the axes.

In the case of a curved preformed archwire as raw material, the preferred embodiment the sequence is as follows:

For Step 1: The moving of the second gripping tool 118 in done in a configuration, so that the rotation and angulation orientation fits to the orientation of the archwire in its initial shape, and then moving the first gripping tool 116 to insert the archwire into the second gripper (translation moves).

For Step 5: Move the first gripping tool to release completely from the wire. Move the second gripping tool so as to align the orientation of the part of the archwire which is going to be gripped by the first gripping tool in the next step in rotation and angulation direction to the X, Y, and Z coordinates of the first gripping tool, rotate the first gripping tool to align the torque orientation of the first gripper (rotation around length axis) to the part of the archwire which is going to be gripped, then move the first gripping tool by translation moves in X, Y, and Z directions to the grip position.

In the case of a straight wire as initial wire shape, step 5 can be reduced to just move the first gripper back along the wire length axis to the new grip position.

For Step 3: It has been found that the movement called for by step 3 should be performed such that a constant distance, equal to the length of the archwire in the starting configuration of the move is maintained between the fixed gripping tool and the moveable gripping tool. This distance should be maintained in order to avoid applying tension or compression to the wire. Since the moveable gripping tools are moving potentially in three dimensions during the bending, the distance that needs to be maintained is measured along the length of the archwire. Such an approach is described in detail in the U.S. patents of W. Butscher et. al. cited previously, the contents of each of which are fully incorporated by reference herein, where Bezier-splines have been used to approximate the bent shape of the wire.

The problem of avoiding tension or compression can also be addressed by adding an additional translation axis and associated fourth prismatic joint to the entire bending machine 108 which is oriented parallel to the X-axis (FIG. 2) which is aligned parallel to the wire length axis $X_w$. Releasing this additional axis allows the wire to be bent without tension or compression. To compensate for deviations of the cumulative length of a wire the actual movement of the fourth prismatic joint in the X direction has to be measured and considered in further movements in step 5 to reposition the grippers. Moreover, the force sensor signals can be monitored during the bending movement. In case of too high forces in wire length direction, compensation movements using the fourth prismatic joint can be defined as to reduce the tension or compression load on the wire. The compensation movements are then also considered in further movements in step 5 to guarantee the overall shape.

The target position of the manipulator movement in step 3 usually does not correspond to the desired bending geometry of the wire. Instead, a certain spring-back effect of the wire must be considered. In general, the target position corresponds to the desired bending position plus a certain amount of overbending. The overbending part depends strongly on the shape of the desired bending position and cannot be predicted theoretically in advance with a sufficient accuracy. To overcome this problem, a concept for overbending wires with elastic-plastic properties has been given in the previously cited U.S. patents of W. Butscher et al. which can be directly used for the herein disclosed bending apparatus, too. The concept bases on a closed-loop-control, which overbends the wire in several loop steps until the required shape is formed. The actual shape of the bend within the loop is detected by moving the manipulator according to force sensor signals in a position where the forces and moments are in the order of the measurement resolution (zero-force-position). The remaining elastic deformation of the wire in this zero-force-position can be neglected and the relative position of the two grippers corresponds to the relative position of the straight wire segments towards each other in the released situation. This zero-force position is compared to the planned bending position. If the difference is bigger than the tolerance limits, an additional bending step follows to decrease the difference.

The above-cited patents to W. Butscher et al. also describe ways to process other wire material like shape-memory-alloys which are ready for adopting at the proposed bending apparatus. Following this approach, these wires are bent within this step 3 of the bending process to the desired bending position and being held by the grippers in this position. Then, the wire segment between the two grippers gets heat-treated by the wire heating device up a certain temperature and for a certain time. The heat-treatment transfers the currently deformed position of the wire segment into the memory of the shape-memory-alloy. After releasing the wire from the grippers, the wire stays at the new shape.

The different ways to bend or shape the wire at a given location also can be split up into a series of different bend locations, if this is needed for reasons like efficiency, stiffness or maintenance. This leads to additional handling requirements of the wire equal to additional time needed. In which way such a bending system will be designed or set up will be driven by the complex configuration of wire geometries to be manufactured.

Manufacturing Environment

FIG. 10 shows an industrial manufacturing cell 1100 which is set up to manufacture customized archwires one after the other continuously, as it would be the case in a precision appliance service center serving a plurality of clinics as shown in FIG. 1.

A plurality of functions for additional features beyond the wire bending machine 108 may be incorporated in such an industrial manufacturing cell 1100 such as:

- A wire handling robot 120 that feeds the wire 122 from a magazine of wires 124 to one of the gripper tools of the manipulators 112 and 114. The robot 120 may take the form of the six-axis wire bending robot with gripping tool (e.g., as shown in FIG. 6 or 6A) at the end of the arm, as described in the previously cited patents of Butscher et al. After the wire bending operation is completed by the wire bending machine 108, the wire handling robot 120 removes the wire from the wire bending machine 108 and transports it to an output station, not shown in FIG. 10, for further processing like marking of the wire and packaging.
- Additional axes or robots to provide a good accessibility for the feeding and removing process. For example, one of the bending manipulators 112 or 114 can be provided with an additional prismatic joint and or revolute joint in order to allow it to be moved to an insertion position to offer enough clearance for the insertion of the wire by the handling robot into one of gripping tools, or manual insertion of one of the wires. An additional axis at one of the bending manipulators 112 or 114 can be envisioned to perform this movement. Such a translational or rotational positioning axis can be designed in order to do a high speed positioning move with limited demands for accuracy, while the bending axes within the manipulators per se are designed for high precision moves in a range of a few millimeters.
- a source of wire raw material, e.g. magazine 124, containing a plurality of straight lengths of the raw material wires, ready to be grasped by the wire handling robot 120.
- a source of raw wire coiled on a spool, not shown in FIG. 10, from which the needed lengths will be taken and before or after the bending process be cut as needed.
- separate bending or shaping tools, not shown in FIG. 10, for geometries that cannot be bent with the main grippers or that are occurring on a non-frequent basis, so that it does not make sense to integrate in the main bending function. The wire handling robot 120 could be used to remove a partly processed wire from the bending apparatus as to forward it to a special device for forming bends which cannot be made by the bending apparatus. Such a device can be a loop bending unit. Such devices are shown in the prior patents of Butscher et al. After finishing the forming process in this device the wire handling robot 120 returns the wire to the bending machine 108 so as to finish the bending process. If such additional tools are used to shape materials requiring a heat treatment step to change its shape, the area used for a positive lock (or better form-closed) needs to be not electrical conductive (i.e. through the use of ceramics) so that the current flows through the area to be reshaped in a controlled way.

if shapes shall be formed requiring additional tools the handling robot 120 can be used as a third manipulator. If, for example an Omega-shaped loop (Ω) must be shaped into the archwire, a straight wire segment of e.g., 20 mm will be hold between the two gripping tools mounted to the bending machine 108, one gripper clamping the wire the other only holding it loose and just leading it. Now, the handling robot 120, equipped with a U-shaped punch at the end of the robotic arm instead of or as part of the gripper tool, moves towards the wire perpendicular to the wire length axis and deforms the wire as needed, leading to the desired Omega-shape. A wide variety of shapes can be produced using this approach.

a marking system, not shown in FIG. 10, to apply marks to the wire to identify the required insertion position in the patient's mouth. Such marks can be designed as a dash across the wire. The marks can be positioned to indicate the midpoint of the wire between two teeth or two brackets or to indicate the mid of selected brackets. The marks can be made with inkjet system or by laser. Especially preferred is laser marking dedicated to create permanent markings on the wire which are visible throughout the time in which the wire is used for treatment of a patient.

a marking system, not shown in FIG. 10, to apply marks to the wire to identify the individual wire itself and manner of insertion into the patient. Such a marking system can apply a data matrix code or a barcode on the wire for example by laser technology. To read these markings special scan-cameras are available (such as the KENDS-system supplied by Ulrich Swiss AG for data matrix code). Such individual marks allow to build up an identification system beginning at wire manufacturing up to the orthodontic practice and avoids mistakes due to wrong packaging or mixing up of the wires after removing them from the package.

a connecting tool, not shown in FIG. 10, to connect wires of different cross-sections or materials by welding, crimping or other common assembly techniques, a cross-section measurement tool, not shown in FIG. 10, to check the dimensional quality of the raw material a labeling system, not shown in FIG. 10, to apply labels to the finished wires as an identifier, a packaging system, not shown in FIG. 10, for putting the wires into a temporary box or into the final box.

a packaging system, not shown in FIG. 10, for putting the wires into an indirect bonding tray equipped with brackets output magazines, not shown in FIG. 10, to collect multiple wires before releasing them from the manufacturing cell, making sure that a wire always is in a unique location to prevent any mismatch of wires;

a conveyor system, not shown in FIG. 10, for automatic handling of the magazines.

Many of the manufacturing features for wires described in the above-cited patents of Butcher et al. are applicable to the features of the manufacturing cell of FIG. 10 and described above, see FIGS. 2 and 32-35 of U.S. Pat. No. 6,612,143 and the associated description, the content of which is incorporated by reference herein.

Alternative Configurations of Manipulators

While a preferred embodiment for the manipulators 102 and 104 is shown in FIGS. 2-4, other designs of the bending machine and in particular the arrangement and combination of the revolute joints and prismatic joints are possible. The driving axes of such joints can be distributed on the two manipulators 112 and 114 in different ways. The minimum requirement is to have at least three rotation axes and three translation axes in order to allow complex bends with six degrees of freedom. In principle even more axes can be used.

If only the minimum required number of three rotation axes and three translation axes is used there are, among others, the following combinations possible:

Combination A: the first manipulator 112 includes three revolute joints defining three rotation axes (preferably but not necessarily mutually orthogonal), and the second manipulator 114 includes the three prismatic joints defining three translation axes (again, preferably but not necessarily mutually orthogonal).

Combination B: the first manipulator includes one revolute joint defining one rotation axis and three prismatic joints defining three translation axes; the second manipulator includes two revolute joints defining two rotation axes.

Combination C: the first manipulator includes two revolute joints defining two rotation axes and one prismatic joint defining one translation axis; the second manipulator includes one revolute joint defining one rotation axis and two prismatic joints defining two translation axes.

Combination D: The bending machine has layout in which that has all three rotation axes and all three translation axes are concentrated on one manipulator, while the other gripper is installed fixed in space.

The preferred alignment of the driving axes according to the principle axes of the gripped wire segments is also not mandatory. In order to manufacture bends described by six degrees of freedom it is sufficient, if at least three rotation axes are not parallel and do not lie in a common plane and in the same way the three translation axes are not parallel and do not lay in a common plane. But this general case with non-perpendicular rotation axes and translation axes causes unfavorable movements of the manipulators in comparison to the case where the rotation axes and the translation axes as well are aligned to form an approximately orthogonal system.

Reduced Complexity of Desired Bending Shape

The aforementioned embodiments are designed to place a six degrees of freedom bend into an archwire and must follow the above described minimum requirements of the number of axes and their alignment. However, if less than six degrees of freedom are desired for the bends, it can be possible to reduce the number of axes.

For example by eliminating the rotation axis α which is aligned to the wire length axis $X_w$ (see FIG. 2, 3), it is possible to place any shape of the bend except for the torque component. Such a reduced embodiment can be useful for example in combination with round wire cross-section, where a torque is not useful.

By further eliminating the rotation axis β which performs the angulation (see FIGS. 2, 4) and the Z translation axis (FIG. 2) which performs movements in vertical direction of the archwire, it is possible to produce so-called planar archwires. These planar archwires have only bends in the plane of the occlusal plane of the archwire and are often used in orthodontic treatments during the initial phase of a treatment.

Thus, one possible implementation of the invention takes the form of a machine (108) for precisely bending an elongate, bendable medical device (e.g., archwire) from an initial shape into a desired new shape, comprising: a revolute joint defining a controlled rotation axis (or optionally two revolute joints); at least three prismatic joints defining a controlled translation axes arranged relatively to each other in such a way that the translation axes are not parallel to each other and the translation axes do not lie in one plane; wherein the revolute joint and at least three prismatic joints are combined in any fashion into a compact bending apparatus comprising a first compact, moveable manipulator 112 and a second separate, compact, moveable manipulator 114, a first gripping tool 116 affixed to the first manipulator and a second gripping tool 118 affixed to the second manipulator, each of said gripping tools having a gripping structure for releasably holding said medical device, wherein the first and second manipulators are arranged in such a way that the first and second gripping tools are able to move relative to each other in four degrees of freedom (or five degrees if the second revolute joint is included); and a control unit operable of the first and second manipulators and the first and second gripping tools so as to form a bend into the medical device.

Although these reduced embodiments are not covered in detail in this description, it must be appreciated that a skilled artisan can easily use the description of the six degrees of freedom embodiment to create such a reduced complexity embodiment.

Wire Tube Processing

As noted above, the bending machine of this disclosure can bend a variety of workpieces. Instead of solid wires, tubes can be used to receive another configuration of mechanical properties that may be beneficial for certain treatment scenarios.

To bend such tubes it is necessary in most cases, to make sure that no buckling will occur. This can be realized by heating the tube while being bent. In another embodiment the tube may be filled with a substance capable of preventing buckling, such as a liquid that is subsequently hardened, or compressed or pressured gas.

Calculation of Axes Movement

In a bending apparatus with a standard industrial 6-axis-robot as known from prior art (see the above-cited patents of W. Butscher et. al.) the desired bending position can be directly transmitted to the controller of the 6-axis-robot. The controller splits up the desired bending position into movements of the respective joints and controls the complete path of motion.

In the case of the bending apparatus disclosed herein, kinematic equations for the two manipulators 112 and 114 are needed in order to calculate the relation between axes movements and movement of the respective gripping tools in space. The relative movement of the two grippers towards each other represents the bending position. Naturally, these equations are applied not only to the bending position (step 3 of the above mentioned manufacturing steps), but also to all other movements such as release, depart and approach movements.

A robotic manipulator (112, 114) can be regarded as a set of links connected to each other by various joints. A robot manipulator with n joints has n+1 links. The joints are referred by an index j=1 . . . n and the links are numbered from j=0 . . . n. Link 0 is attached to the base and fixed. To perform the kinematic analysis a coordinate system is attached to each link. A common systematic approach to assign the coordinate system is the Denavit-Hartenberg-convention. See Denavit, J., Hartenberg, R. S.: A kinematic notation for lower pair mechanisms based on Matrices. Journal of Applied Mechanics, vol. 77, pp. 215-221, June 1955, the content of which is incorporated by reference herein.

By this convention the z-axis of the coordinate system is aligned to the rotation axis of revolute joints. For prismatic joints the z-axis is aligned to represent the positive movement direction.

The transition from link (j−1) to the next link (j) is described by a homogenous transformation. If the coordinate systems are defined according Denavit-Hartenberg convention this transformation has the general form $$_{j}^{j-1}A = \begin{bmatrix} \cos\theta_j & -\sin\theta_j\cos\alpha_j & \sin\theta_j\sin\alpha_j & a_j\cos\theta_j \\ \sin\theta_j & \cos\theta_j\cos\alpha_j & -\cos\theta_j\sin\alpha_j & a_j\sin\theta_j \\ 0 & \sin\alpha_j & \cos\alpha_j & d_j \\ 0 & 0 & 0 & 1 \end{bmatrix} \quad (1.)$$

The manner of obtaining a complete transformation from the base system to the gripping point of the gripping tools is calculated by multiplying all the single joint transformations to obtain a final transformation matrix T. This matrix T describes the relation between the joint values and the position and orientation of the gripping point of the gripping tool with respect to a fixed base system (i.e., the direct kinematics). This matrix can be obtained by persons skilled in the art from the foregoing description and the disclosure of the Denavit et al. paper cited above.

In practical realizations of the bending machine of this disclosure, there might be small deviations of the axes from the exact orthogonal alignment, although orthogonal alignment was planned by design. If these deviations are detected by means of calibration and proper link parameters have been set up, the formula for direct kinematics reflects the actual behavior of the manipulators. However the previously explained approach for transforming a bending position into the subspace of the manipulator and the calculation of the joint values does not return precise results.

In the case of small deviations from the orthogonal alignment, this approach is still usable. The joint values are then calculated within an iterative loop. In an initial run the joint values are calculated based on the planned bending position. Then the actual achieved bending position is calculated and compared to the planned bending position. If the difference is greater than a limit, then a new target position is defined by adding a compensation movement to the planned bending position. The joint values for this target position are then evaluated the same way and the actual achieved bending position is recalculated.

Although the orthogonal alignment of the axes—or at least close to orthogonal—represents the preferred way of design for this bending apparatus, other designs are possible with non-orthogonal axes systems. In this case the necessary mathematics gets more complicated but there is no principle change in the described approach. The process to split up a general bending position into three given rotation axes with arbitrary orientation can be found in literature. See: J.

Wittenburg and L. Lilov: "Decomposition of a Finite Rotation into Three Rotations about Given Axes", published in Journal Multibody System Dynamics by Springer Netherlands ISSN1384-5640 (Print) 1573-272X (Online) Issued in Volume 9, Number 4/May, 2003 DOI 10.1023/A:1023389218547 Pages 353-375), which is incorporated by reference.

Because the described way to solve inverse kinematics just by comparing coefficients is not valid for other than orthogonal alignment, numerical approaches are available to solve such systems. See, for example: Anthony A. Maciejewski and Charles A. Klein: "The Singular Value Decomposition: Computation and Applications to Robotics," published in: The International Journal of Robotics Research, Vol. 8, No. 6, 63-79 (1989), DOI: 10.1177/027836498900800605), which is incorporated by reference.

Calibration

If calibration is desired to achieve even higher levels of accuracy, or to check and adjust the setup of the assembly, the proposed kinematic layout of the machine greatly simplifies this task.

To calibrate the proposed bending core, a certain axis movement can be carried out and the actual movements of the wire are monitored with a camera system. By comparing the desired movement and the actual movement the precise position and orientation of the driving axis can be determined. Based on the precise positions and orientations for all axes a real model of the bending core can be developed. The necessary movements can then be calculated based on this real model.

The following clauses are considered further descriptive of the disclosed inventions:

1. A machine for precisely bending an elongate, bendable medical device (e.g., archwire 122) from an initial shape into a desired new shape, comprising:

at least three revolute joints (208, 210, 212) defining controlled rotation axes ($\alpha$, $\beta$, $\gamma$) arranged relatively to each other in such a way that none of the rotation axes are parallel and the rotation axes do not lie in one plane;

at least three prismatic joints (202, 204, 206) defining controlled translation axes (X, Y, Z) arranged relatively to each other in such a way that the translation axes are not parallel to each other and the translation axes do not lie in one plane;

wherein the at least three rotational joints and at least three linear drives are combined in any fashion into a compact bending apparatus (108) comprising a first compact, moveable manipulator (112) and a second separate, compact, moveable manipulator (114), a first gripping tool (116) affixed to the first manipulator and a second gripping tool affixed to the second manipulator (118), each of said gripping tools having a gripping structure (FIG. 7) for releasably holding said medical device, wherein the first and second manipulators are arranged in such a way that the first and second gripping tools are able to move relative to each other in six degrees of freedom; and a control unit (110) operable of the first and second manipulators and the first and second gripping tools so as to form a bend into the medical device.

2. The machine of clause 1, wherein the initial shape of the medical device is straight.

3. The machine of clause 1, wherein the initial shape of medical device is curved in one plane.

4. The machine of any of clauses 1-3, wherein the medical device comprises an orthodontic archwire.

5. The machine of any preceding clause, further comprising a handling robot (120, FIGS. 1, 11) supplying medical devices to be bent to one of the first and second gripping tools.

6. The machine of any preceding clause, further comprising a vision system (1102, and/or 1104 FIG. 10) monitoring the movements of the manipulators and the shape of the medical device before and after bending.

7. The machine of any preceding clause, wherein the medical device comprises a medical device selected from the group consisting of a prosthesis, and orthopedic device, an implant, a stent, a fixation plate, a spectacle frame, and a surgical tool.

8. The machine of any preceding clause, wherein the first manipulator comprises three linear drives arranged in X, Y, Z orthogonal coordinate system and a single rotational joint (FIGS. 2, 3); and wherein the second manipulator comprises two rotational joints (FIGS. 2, 4).

Figure 7:
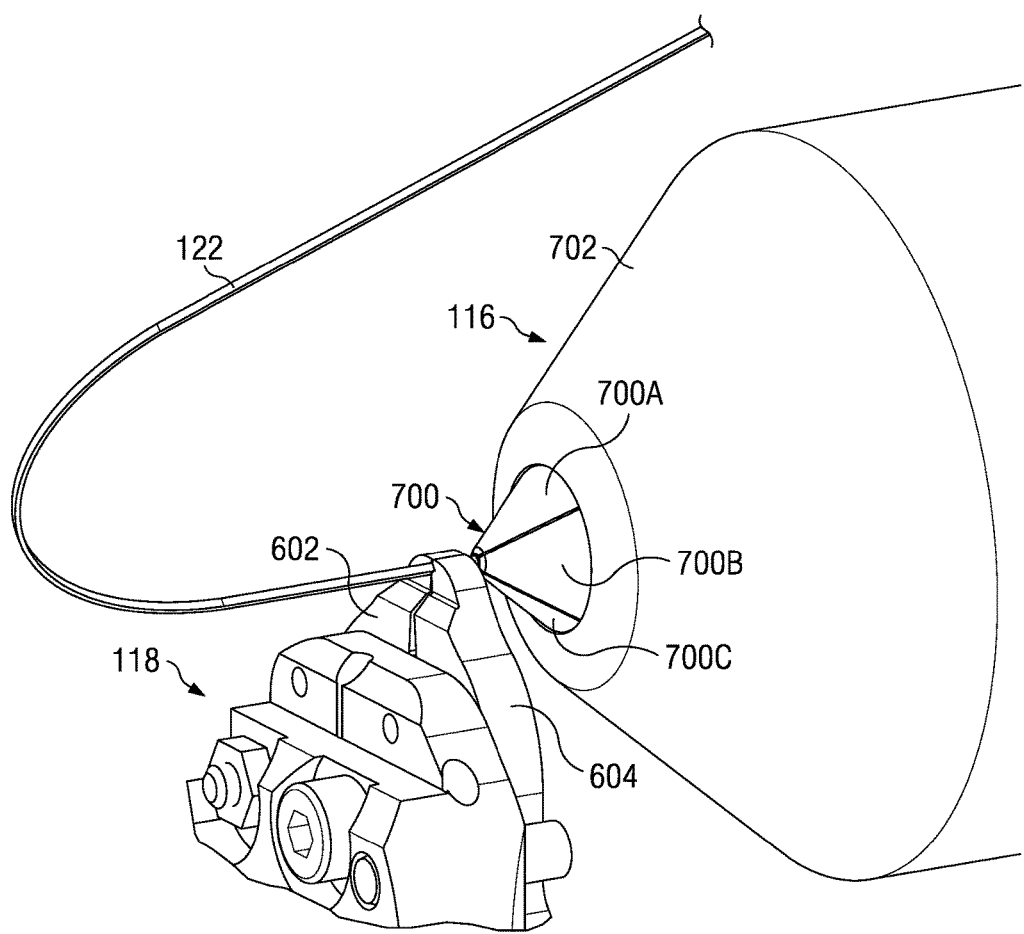
FIG. 7 is an illustration of first and second gripping tools holding an orthodontic archwire, where one gripping tool is shaped in the form of a collet and the other gripping tool is of the configuration shown in FIG. 6.

9. The machine of any preceding clause, wherein the first gripping tool affixed to the first manipulator comprises a collet and wherein the second gripping tool affixed to the second manipulator comprises a pair of opposed gripping fingers (FIG. 7).

10. The machine of clause 8, wherein the medical device defines a longitudinal axis, and wherein the first manipulator is rotatable about the longitudinal axis of the medical device while gripping the medical device.

11. The machine of clause 8, wherein the two rotational joints of the second manipulator coincide with cross-sectional axes of the medical device.

12. The machine of any preceding clause, further comprising a means for heating the gripping tools above ambient temperature.

13. The machine of any preceding clause, further comprising a force measurement system coupled to the first and second gripping tools (FIG. 6A) for measuring forces imparted by the medical device to the bending machine.

14. The machine of any preceding clause, wherein one of the gripping tools comprises gripping fingers and wherein the gripping fingers are incorporated into a gripping plate unit (601, FIG. 6).

15. The machine of any preceding clause, wherein one of the gripping tools comprises gripping fingers (FIG. 7) and wherein the gripping tool is equipped with an electromechanical actuator which supports a controllable opening movement, including a partial opening of the gripping fingers.

16. The machine of clause 16, wherein the partial opening permits the medical device to slip through the gripping features without losing contact between the medical device and the gripping fingers during such slipping.

17. The machine of any preceding clause, wherein one of the gripping tools comprises gripping fingers and wherein the gripping fingers comprise an edge defining a bending contour (FIGS. 9B, 9C).

18. The machine of clause 17, wherein the bending contour comprises a groove having a curved surface.

19. The machine of any preceding clause, further comprising a heating system for heating the medical device while it is being bent by the bending machine.

20. The machine of clause 19, wherein the heating system comprises a power supply providing an electrical current to the medical device through the first and second gripping tools 116 and 118.

21. The machine of clause 6, wherein the medical device comprises a longitudinal axis and first and second cross-sectional axes, and wherein the vision system comprises a camera oriented so as to view the medical device along one of the cross-sectional axes (FIG. 10).

22. The machine of clause 21, wherein the medical device comprises an orthodontic archwire having a longitudinal axis X, a rectangular cross-section having axes Y and Z, and wherein the visional system comprises a camera oriented so as to view the archwire along the Y ax (FIG. 10, vision system component 1104).

23. The machine of clause 21, wherein the medical device comprises an orthodontic archwire (122); wherein the archwire is made from a shape memory alloy, and wherein the control unit is (1) operable of the first and second manipulators and first and second gripping tools to grip the archwire and move it to an approximate straight condition, and (2) operable of the vision system to scan the shape of the archwire after it has been released from one of the first or second manipulators to resume a shape previously formed in the archwire by the bending apparatus.

24. The machine of clause 21, wherein the vision system comprises an camera operable to obtain an infrared image of the medical device while being held by the bending apparatus.

25. A method of bending a medical device, comprising:
providing a compact bending apparatus comprising a first compact, moveable manipulator and a second separate, compact, moveable manipulator, the bending apparatus including a first gripping tool affixed to the first manipulator and a second gripping tool affixed to the second manipulator, each of said gripping tools having a gripping structure for releasably holding said medical device, wherein the first and second manipulators are constructed and arranged in such a way that the first and second gripping tools are able to move relative to each other in six degrees of freedom;
gripping the medical device by the first and second gripping tools;
precisely controlling the movement of the first and second gripping tools and the first and second manipulators so as to form a bend and/or twist in the medical device.

26. The method of clause 25, further comprising the step of heating the first and second gripping tools above ambient conditions while forming the bend and/or twist in the medical device.

27. The method of clause 25 or 26, further comprising the step of heating the medical device above ambient conditions while forming the bend and/or twist in the medical device.

28. The method of clause 27, further comprising the step of generating an infrared image of the medical device while forming the bend and/or twist in the medical device.

29. The method of clause 27, wherein the medical device comprises an orthodontic archwire.

30. The method of clause 29, wherein the archwire is made from a shape memory alloy.

31. The method of clause 29, further comprising the steps of: forming a multitude of bends and/or twists in the archwire so as to form a completed archwire, substantially straightening the wire, allowing the wire to come to a relaxed condition, and then measuring the shape of the wire with a vision system.

32. The method of any preceding clause, further comprising the step of measuring the shape of the medical device with a vision system.

33. The method of clauses 25-31, wherein the medical device comprises an orthodontic archwire having a longitudinal axis X, a rectangular cross-section having axes Y and Z, and wherein the visional system comprises a camera oriented so as to view the archwire along the Y axis.

34. A bending apparatus as described in any of clauses 1-25 except that the bending apparatus is in the form of a reduced complexity bending apparatus with three prismatic joints and either one or two revolute joints combined and arranged into two separate compact manipulators each equipped with a gripping tool.

35. The bending apparatus of clause 34, wherein the first manipulator includes the three prismatic joints and wherein the second compact manipulator includes the one or two revolute joints.

While a number of exemplary aspects and embodiments have been discussed above, those of skill in the art will recognize that modifications, permutations, additions and sub-combinations thereof are present in this disclosure. It is therefore intended that the following appended claims and claims hereafter introduced are interpreted to include all such modifications, permutations, additions and sub-combinations as are within their true spirit and scope.

We claim:

1. A method of calibrating a bending apparatus comprising at least a first moveable manipulator and at least a second moveable manipulator, comprising the steps of:
positioning a wire such that the wire is held by a bending core comprised of the first moveable manipulator and the second moveable manipulator;
(a) moving a first axis of the first moveable manipulator
(b) measuring a resulting movement of the wire,
repeating steps (a) and (b) for each of a plurality of axes of each of the first moveable manipulator and the second moveable manipulator and measuring the resulting movement of the wire, wherein each of the plurality of axes are moved in different directions;
recording each movement of each of the plurality of axes of each of the first moveable manipulator and the second moveable manipulator and recording each corresponding measured resulting movement of the wire;
comparing the recorded movements of the wire to desired movements of the wire to determine positions and orientations of each of the plurality of axes;
developing a real model of the bending core based on the positions and orientations of each of the plurality of axes, thereby calibrating the bending apparatus.

2. The method of claim 1, wherein at least one of the plurality of axes are moved in a translational direction.

3. The method of claim 1, wherein at least one of the plurality of axes are moved in a rotational direction.

4. The method of claim 1, wherein the plurality of axes are moved in translational and rotational directions.

5. The method of claim 1, wherein the resulting movements of the wire are measured by a vision system.

6. The method of claim 5, wherein, the vision system is configured to measure single bends in the wire as soon as they are made.

7. The method of claim 6, wherein the wire is made from an alloy.

8. The method of claim 5, further comprising iteratively bending and measuring bends in the wire until correct over-bending values are found.

9. The method of claim 8, wherein the wire is made from an alloy.

* * * * *